(12) United States Patent
Nicolopoulos et al.

(10) Patent No.: US 8,253,099 B2
(45) Date of Patent: Aug. 28, 2012

(54) METHODS AND DEVICES FOR HIGH THROUGHPUT CRYSTAL STRUCTURE ANALYSIS BY ELECTRON DIFFRACTION

(75) Inventors: Stavros Nicolopoulos, Valencia (ES); Daniel Bultreys, Brussels (BE); Edgard Rauch, Champagnier (FR)

(73) Assignee: NanoMegas SPRL, Molenbeek-Saint-Jean (BE)

( * ) Notice: Subject to any disclaimer, the term of this patent is extended or adjusted under 35 U.S.C. 154(b) by 0 days.

(21) Appl. No.: 13/127,455

(22) PCT Filed: Nov. 6, 2009

(86) PCT No.: PCT/EP2009/064726
§ 371 (c)(1),
(2), (4) Date: May 3, 2011

(87) PCT Pub. No.: WO2010/052289
PCT Pub. Date: May 14, 2010

(65) Prior Publication Data
US 2011/0220796 A1     Sep. 15, 2011

Related U.S. Application Data

(60) Provisional application No. 61/112,036, filed on Nov. 6, 2008.

(30) Foreign Application Priority Data

Nov. 6, 2008 (EP) ..................................... 08168475

(51) Int. Cl.
*H01J 37/28*     (2006.01)

(52) U.S. Cl. ......................................... 250/307; 250/311
(58) Field of Classification Search .................. 250/307, 250/306, 311
See application file for complete search history.

(56) References Cited

U.S. PATENT DOCUMENTS

| | | | | |
|---|---|---|---|---|
| 6,448,556 B1 * | 9/2002 | Cowley et al. | ................. | 250/311 |
| 2010/0108882 A1 * | 5/2010 | Zewail | ......................... | 250/307 |
| 2010/0108883 A1 * | 5/2010 | Zewail | ......................... | 250/307 |

FOREIGN PATENT DOCUMENTS

| WO | WO 2005/022582 A | 3/2005 |
|---|---|---|
| WO | WO 2008/060237 A | 5/2008 |

OTHER PUBLICATIONS

Du, et al., "Measurement of crystal thickness and orientation from selected-area Fourier transformation of a high-resolution electron hologram," *Micron, Pergamon*, (Jan. 1, 2006) 37:1, 67-72.

Vincent, et al., "Double conical beam-rocking system for measurement of integrated electron diffraction intensities," *Ultramicroscopy*, (Mar. 1, 1994) 53:3, 271-282.

(Continued)

*Primary Examiner* — Kiet T Nguyen
(74) *Attorney, Agent, or Firm* — Knobbe, Martens, Olson & Bear, LLP

(57) ABSTRACT

A method and device for electron diffraction tomography of a crystal sample, which employs scanning of the electron beam over a plurality of discrete locations of the sample, in combination with a beam scanning protocol as the beam converges at every discrete location (42, 43) of the sample (38) to obtain a series of electron diffraction patterns, use of template matching to determine crystal orientations and thickness maps to obtain a common intensity scaling factor.

13 Claims, 19 Drawing Sheets

OTHER PUBLICATIONS

Figure 1:
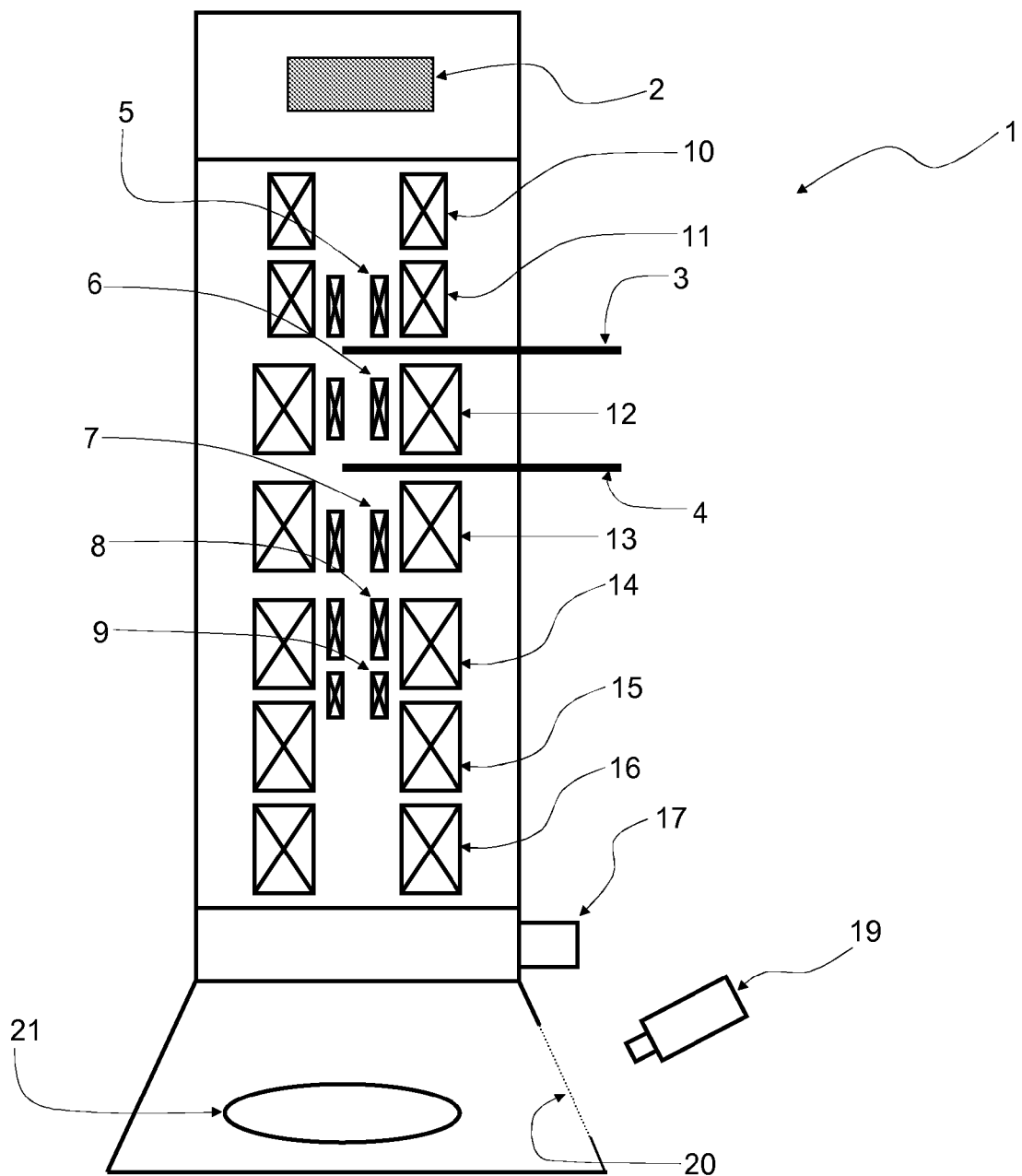

Dudka, et al., "Crystal structure refinement using Bloch-wave method for precession electron diffraction," *Ultramicroscopy*, (Feb. 25, 2007) 107:6-7, 474-482.

Ciston, et al., "A quantitative analysis of the cone-angle dependence in precession electron diffraction," *Ultramicroscopy*, (May 1, 2008) 108:6, 514-522.

International Search Report issued in corresponding PCT Application No. PCT/EP2009/064726, mailed Feb. 8, 2010.

International Preliminary Report on Patentability issued in corresponding PCT Application No. PCT/EP2009/064726, mailed Jan. 31, 2011.

\* cited by examiner

Crocidolite (A)

Index = 1242

(B)

Chrysotile (C)

Index = 550

(D)

(E)

(A)  (B)

(C)  (D)

(A) (B)

METHODS AND DEVICES FOR HIGH THROUGHPUT CRYSTAL STRUCTURE ANALYSIS BY ELECTRON DIFFRACTION

RELATED APPLICATIONS

This application is the U.S. National Phase filing under 35 U.S.C. §371 of PCT/EP2009/064726, filed Nov. 6, 2009, entitled "METHODS AND DEVICES FOR HIGH THROUGHPUT CRYSTAL STRUCTURE ANALYSIS BY ELECTRON DIFFRACTION", which designated the United States and was published in English as WO2010/052289 on May 14, 2010, which claims priority to European Patent Application No. 08168475.5, filed Nov. 6, 2008, and U.S. Provisional Application No. 61/112,036, filed Nov. 6, 2008. The entire contents of these priority applications are incorporated herein by reference.

FIELD OF THE INVENTION

The present invention is in the field of determination of crystal structure characteristics, such as internal three dimensional structure, crystal orientation, phase, and thickness by an electron diffraction analyzer, using techniques that are suitable for high-throughput structural analysis, and which can be applied to crystals having dimensions in the nanometer range.

BACKGROUND

High throughput X-Ray powder screening of materials for useful properties reduce development times by up to orders of magnitudes, at a fraction of costs. For example, ability to unequivocally differentiate one crystallographic phase from another has proven to be the greatest asset in the pharmaceutical field: powder X-Ray diffraction patterns of each crystalline form contain characteristic sets of peaks unique to that form, allowing the patterns to be used as fingerprints. Fully automatic powder crystal data evaluation may allow speedy (pattern analyzed in minutes) and cost effective handling of big amount of information obtained. Such high throughput techniques have strong impact on quality control of industrial products.

In many modern scientific and industrial applications, it is necessary to be able to study samples at the nanometer scale, where most materials are ordered, often crystalline. Their physical properties depend on the crystal structure. Unfortunately, the traditional method for atomic structure determination, X-ray crystallography, cannot be used for single crystals with sizes in the nanometer range, either because the limit size for single crystal structure determination with modern Synchrotron sources is above 5 microns, or because powder X-Ray patterns show extremely poor resolution (e.g. peak broadening and overlapping) at decreasing crystallite size (nm). This simple fact limits the contribution of X-ray crystallography and consequently to any attempt of high throughput analysis to nanoscience, a scientific area crucial in many fields, from semiconductors to pharmaceuticals and proteins. Therefore, compounds that only exist at nanocrystalline state are usually out of reach for the X-ray diffraction methods of structure determination and as a result, such nanostructures, despite their given importance, are unknown. The resulting lack of knowledge on the underlying structure-property relationships often prohibits breakthrough developments in a whole research sector or may cause fatal delays in the cycle of further product development.

The resulting lack of knowledge of the underlying structure-property relationships often prohibits breakthrough developments in a whole research sector, or may cause fatal delays in the cycle of further product development.

Electron diffraction (ED) is the method of choice to solve the structural problems at nanocrystal size, as electrons interact about $10^3$ to $10^4$ times stronger with matter than X-rays and, therefore, are ideal for ED of crystals in the nanometer sized range. Nanocrystalline samples can be studied both by electron microscopy and electron diffraction. Transmission electron microscopy (TEM) which uses an electron beam in transmission mode, gives a direct image of the structure, but suffers from lens distortions and limited resolution. This is contrary to the use of an electron beam in electron diffraction techniques which can go to very high resolution e.g. 0.5 Ångström or even higher, but suffer from dynamic scattering. However, it is currently not possible to use ED intensities directly (unlike X-Ray techniques) to solve crystal structures; these drawbacks currently limit general use of ED as reliable technique for nanocrystal structure analysis.

Solving the three dimensional structure of any nanocrystal requires collection of 3 dimensional (3D) intensity data from as many zone axes (ZA) as possible from the same crystal. For many, less symmetrical structures e.g. monoclinic, triclinic crystals, it is important to tilt the crystal to obtain such ZA through a wide range of angles (for example from −40° to 40°). Conventional TEM used in diffraction mode do not always allow high-tilt angles due to restrictions caused by the geometry of the specimen holder and polepiece gap of the objective lens. This causes severe limitations in the attainable resolution of the 3D data, (missing cone problem). As a consequence, 3D data acquisition for any nanocrystal is an extremely time-consuming task—it may take up to days even for experienced researchers to obtain a good quality data set—which makes the method highly unattractive and inappropriate for routine investigations. The situation becomes even worse when studied nanocrystals are electron beam sensitive organics; in that case, even when low dose conditions such as cryo-cooling are applied to minimise beam damage, beam sensitivity makes it impossible to conserve crystal structural integrity for more than few minutes/seconds, making therefore the whole time-consuming standard procedure of single crystal orientation and data acquisition (that normally lasts tens of minutes) difficult or impossible.

Thus, traditional TEM ED data collection techniques are generally limited; the standard procedure is very time consuming, it does not allow collection of a complete 3D-ED intensities on the same single crystal and the diffraction intensities which carry information about the crystal structure are of poor quality, due to multiple/dynamical scattering of the electrons.

In this context, the electron diffraction precession method (EDPM) developed by Roger Vincent & Paul Midgley (Vincent R., Midgley, P. Double conical beam-rocking system for measurement of integrated electron diffraction intensities. *Ultramicroscopy* 53:271-282, 1994) plays a vital role, since it made it possible for the first time significantly to reduce dynamic diffraction effects. In this technique the electron beam is tilted by a small angle, typically 1-3 degrees, and then rotated around the TEM optical axis. In this way a volume of reciprocal space is recorded (integration over excitation error), and more importantly, the multiple/dynamic scattering is greatly reduced, since only a small number of reflections are excited at any time.

An alternative technique for collecting complete 3D electron diffraction data from single nanocrystal, known as electron diffraction rotation method (EDRM), has been proposed (PCT/SE2007/050853) which also reduces the multiple/dynamic scattering. Electron rotation can be achieved by a device rather similar to the one that achieves electron precession. The main difference is that the electron beam does not rotate a circle, but rather follows a straight line, like a pendulum. This line can be along the x-direction, along the y-direction or along any diagonal in between. In order to handle partially recorded reflections, the data must be collected in a number of small angular steps. For example, each scan may have a rotation of only +/−0.5 degrees along a line. The next scan will follow on from exactly where the previous stopped, i.e. from +0.5 to +1.5 degrees, with the next one +1.5 to +2.5 degrees and so on. One such series of rotation patterns can total up to about 6 degrees; the exact range is limited by the design of the specific model of electron microscope, then the crystal will be tilted by a few degrees and the data acquisition will start again. This way, a complete 3D diffraction set may be obtained in diffraction tomography-like mode. Such device for EDRM can rotate the electron beam by a predetermined but variable angular rotation range, and along any direction.

However, one of the drawback of the EDRM technique and the aforementioned EDPM technique is that tilting simultaneously through the whole angular range for 3D data collection and aligning the TEM holder is a very time consuming procedure In addition, due to electron beam sensitivity for crystals useful in pharmaceutical industry and protein nanocrystals, even under low dose conditions and LN2 cooling, only a limited number of ED patterns (e.g. 1-3) can be obtained from each crystal. Moreover, both EDPM and EDRP techniques rely on 3D diffraction data collection by manual or automatic (through computerized TEM holders) tilts of a particular single nanocrystal around a selected crystallographic axis.

An automated electron diffraction tomography procedure (ADT) has been developed which combines nanobeam ED and STEM imaging using a high angular annular dark field detector (HAADF); the use of the latter detector permits a significant reduction in beam damage in comparison with more conventional approaches to diffraction. With ADT, a typical approach during experimental work is to find a suitable crystal, select it with a marker (spot or allowed area) and tilt it, according to a given sequence, around the goniometer axis; there is no need for crystallographic axis to be oriented along the goniometer axis. Automated data processing routines provide automated cell parameter determination after a peak search. Resulting (partial) 3D diffraction data network allows the detection of crystal cell, effects such as partial disorder, twinning, polymorphs and superstructures; measuring ED intensities, even from non-complete ED network may allow to solve individual crystal nanostructures. However, ADT is equally time consuming technique as previous EDPM and EDRM techniques.

It is clear from the prior art that techniques of the art for nanocrystal structure analysis based on electron diffraction are time consuming and use long exposure protocols to obtain full range of tilt angles. A more time-efficient procedure is necessary, which lends itself well to high throughput measurement.

SUMMARY OF THE INVENTION

One embodiment of the invention is a method for electron diffraction tomography of a crystal sample, comprising the steps of:

a) providing a sample (38) comprising a plurality of said crystals (36) in random orientations, b) obtaining an electron diffraction, ED, pattern (44, 46) from each of a plurality of discrete locations (42, 43) within an area of the sample (38), wherein the electron beam used to obtain the ED patterns is scanned across the sample (38), in combination with a beam scanning protocol as the beam converges at every discrete location (42, 43) of the sample (38), c) determining different crystal orientations in the sample using template matching (49) applied to the individual ED patterns (44, 46) obtained in b), d) determining, from relative thickness maps obtained as virtual bright field, STEM bright field, HAADF or zero loss EELS thickness maps, the relative crystal thickness at the discrete location wherein the ED pattern were obtained (42, 43), e) determining a common intensity scaling factor, from the relative thickness determined in d), and normalizing the intensities of individual ED patterns from discrete locations (42, 43), f) calculating (66), from the three dimensional set of normalized ED patterns and orientation information, the atomic crystal structure of the randomly oriented crystals.

One embodiment of the invention is a method as described above wherein the scanning of the electron beam across the sample and hence the discrete locations, in combination with the scanning protocol is achieved using deflection coils in the TEM situated before the sample to scan the electron beam in combination with similar descanning of the ED pattern by means of defection coils situated after the sample.

Another embodiment of the invention is a method as described above, wherein the scanning protocol of the electron beam is in a beam precession protocol or a beam rotation protocol, or any scanning mode protocol leading to a quasi-kinematical diffraction pattern.

Another embodiment of the invention is a method as described above, wherein the discrete locations form an array, and each array element is exposed by sequential displacements of the electron beam.

Another embodiment of the invention is a method as described above, wherein ED patterns that do not belong to crystals of the same phase, are not used in step f).

Another embodiment of the invention is a method for calculating an orientation and phase map of a sample (38) comprising a plurality of crystals (36) in different orientations and different known phases comprising the steps of:

a) providing a sample (38) comprising a plurality of said crystals (36) in different orientations, b) obtaining an electron diffraction pattern (44, 46) from each of a plurality of discrete locations (42, 43) within an area of the sample (38), wherein the electron beam used to obtain the electron diffraction pattern is scanned (30) in precession mode protocol, or other protocols as defined above, such that it converges at the discrete location of the sample (38), in combination with a similar descanning (34) after the sample (38), c) determining the crystal orientations using template matching applied to the individual diffraction patterns (45, 46) obtained in b), d) determining the presence of different crystals phases by using template matching applied the individual diffraction patterns (45, 46) obtained in b), and e) calculating an orientation map and phase map of crystals in the sample from the determination of step c).

Another embodiment of the invention is a device for interfacing with a TEM, configured to adapt said TEM to obtain an ED pattern (44, 46) from each of a plurality of discrete locations (42, 43) within an area of a sample (38) of crystals, and to scan the electron beam used to obtain the ED pattern across the sample (38), in combination with a beam scanning protocol as the beam converges at every discrete location (42, 43) of the sample (38).

Another embodiment of the invention is a device as described above, wherein the TEM comprises deflection coils situated before the sample and defection coils situated after the sample, and the device is configured to activate deflection coils in the TEM situated before the sample to scan the electron beam in combination with similar descanning of the ED pattern by means of defection coils situated after the sample.

Another embodiment of the invention is a device as described above, further comprising a scanning signal generator, configured to provide signals for scanning of the electron beam over said across the sample and wherein function generators are configured to provide signals for the scanning protocol.

Another embodiment of the invention is a device as described above, further comprising a digital camera, or optical CCD camera configured to capture ED patterns projected onto a fluorescent screen in TEM Another embodiment of the invention is a device as described above, further comprising a computer having a computer readable storage means, configured to control movements by the electron beam and to perform template matching for determining crystal orientation and phase, by comparing a recorded ED intensity pattern with simulated templates for all possible crystal orientations and phases and determining the best match.

Another embodiment of the invention is a device for interfacing with a TEM, configured to adapt said TEM for performing in a method as described above.

Another embodiment of the invention is a method and a device therefor, as described above, further comprising additional/alternative identification/fingerprinting of individual grains/crystallites using plots containing experimental precession quasi-kinematical intensities and crystal spacings, which are compared with a crystal data Bank data such as COD, ICDD, FIZ etc. . . . .

Another embodiment of the invention is a method and a device as described above where enhanced identification/fingerprinting of individual grains/crystallites and better quality orientation phase maps are obtained by combining beam scanning according to the method described above with ED energy filtering.

Another embodiment of the invention is a method and a device as described above all type of nanomaterials are fingerprinted and their crystal structure solved at high throughput rates—including beam sensitive organics without necessarily using specimen cryopreservation techniques—as fast scanning through the crystals prevents from crystal degradation and subsequent ED pattern quality loss.

FIGURE LEGENDS

FIG. 1 Cross-section through a transmission electron microscope (TEM) suitable for structural studies according to the techniques of the invention.

FIGS. 2A to F Steps of determining an orientation map of a sample of crystals using an electron diffraction analyzer of the invention comprising a TEM operating in scanning and displacement modes, and template matching.

FIGS. 3A to D Steps of determining a thickness map of a sample of crystals using a electron diffraction analyzer of the invention comprising a TEM operating in scanning and displacement modes.

FIGS. 4A to I Steps of determining the three dimensional crystal structure of a crystal in a sample using a electron diffraction analyzer of the invention comprising a TEM operating in scanning and displacement modes and template matching.

FIGS. 5A to E An example of the steps of template matching to determine the orientation of crystals in a sample of nanocrystalline copper.

FIGS. 6A to H An example of the steps of template matching to determine the orientation of crystals in a sample of asbestos fiber crystals when scanning (with precession) is not used (A) compared with when it is used (F).

FIGS. 7A to H A further example of the steps of template matching to determine the orientation of crystals in a sample of asbestos fiber crystals when scanning (with precession) is not used (A) compared with when it is used (F).

FIGS. 8A to E An example of the steps of template matching to determine the correct phase of asbestos crystals in a sample of asbestos fiber crystals.

Figure 9:
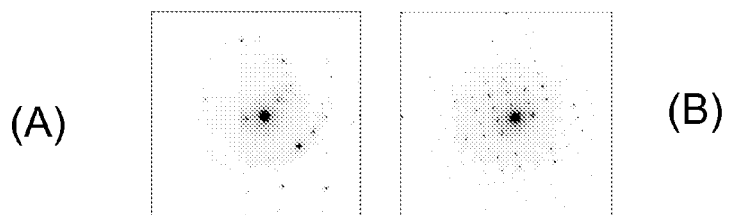

FIGS. 9A and B A comparison of ED patterns obtained from a mayenite crystal $Ca_{12}Al_{14}O_{33}$ in arbitrary orientation when scanning (with precession) of the ED beam and pattern is not used (FIG. 9A) compared with when it is used (FIG. 9B).

FIGS. 10A to D Orientation map and thickness maps (virtual Bright field map) of a sample of mayenite crystals measured according to the methods of the invention, when scanning (with precession) is not used (A) and used (C)

Figure 11:
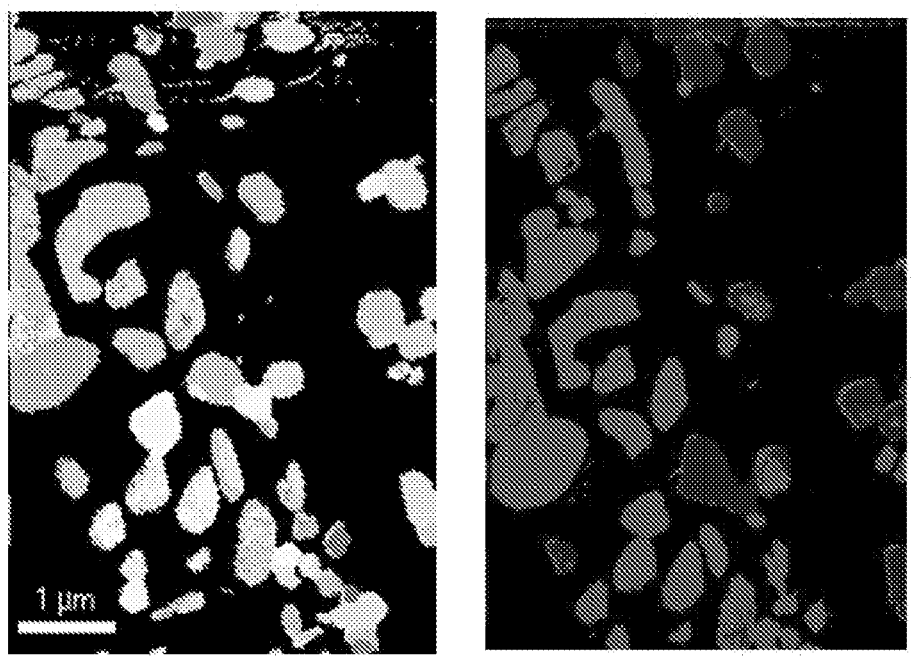
Figure 11:
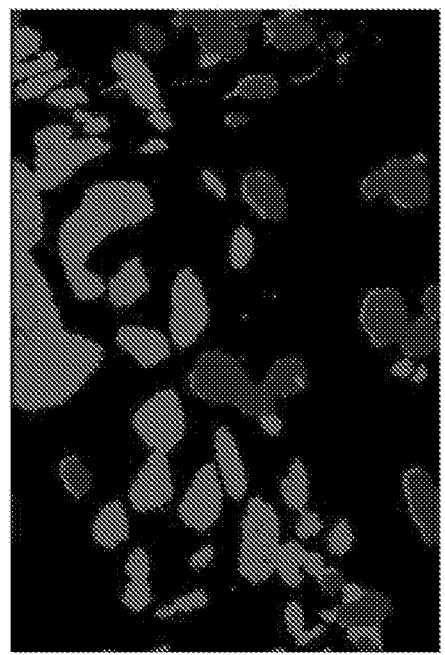

FIGS. 11A to C Orientation map (A) and phase map (B) obtained from a sample of 430 stainless steel containing precipitates of carbide M23C6 and hexagonal nitride $Cr_2N$, where scanning (with precession) was not used (A,B) and used (C)

Figure 12:
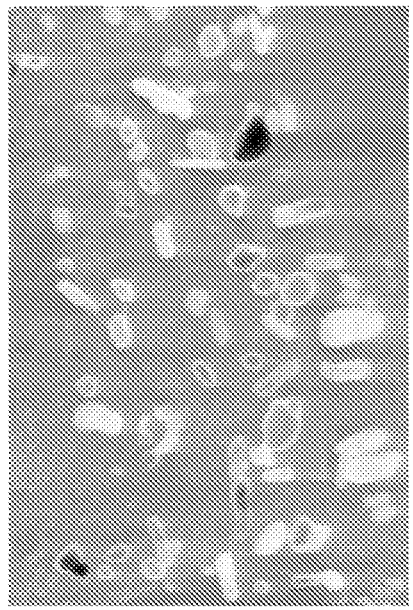
Figure 12:
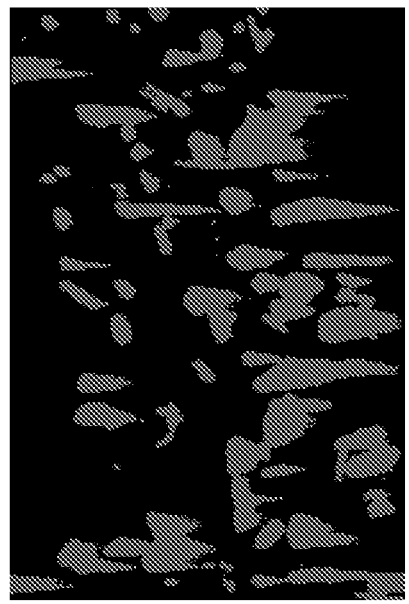
Figure 12:
Figure 12:
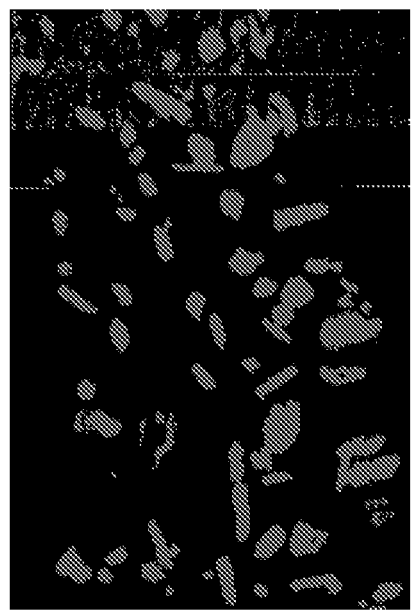

FIGS. 12A to D Remanence effect on a virtual Bright field map (FIG. 12A) and correlation index map (FIG. 12B), effect of subtracting a percentage of the previously acquired ED pattern (FIG. 12C), filtering the index correlation map above a threshold value (FIG. 12D).

Figure 13:
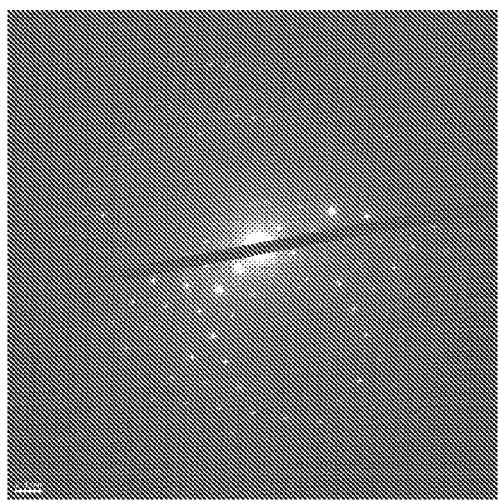
Figure 13:
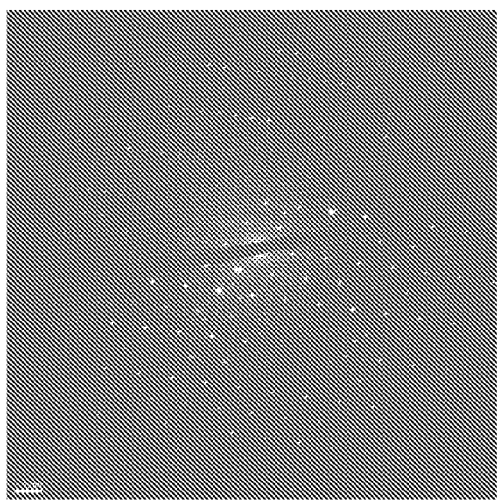

FIGS. 13A to B ED pattern obtained from a mayenite crystal in an arbitrary orientation acquired using a TEM in precession mode without (FIG. 13A) and with (FIG. 13B) an energy filter.

FIGS. 14 to 18 show possible arrangements of electron diffraction device (e.g. a TEM) and associated devices that permit use in a method of the invention.

Figure 19:
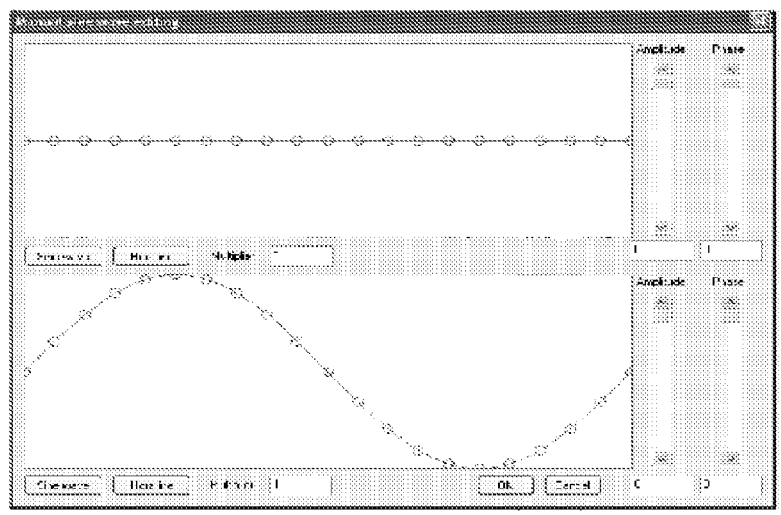
Figure 19:
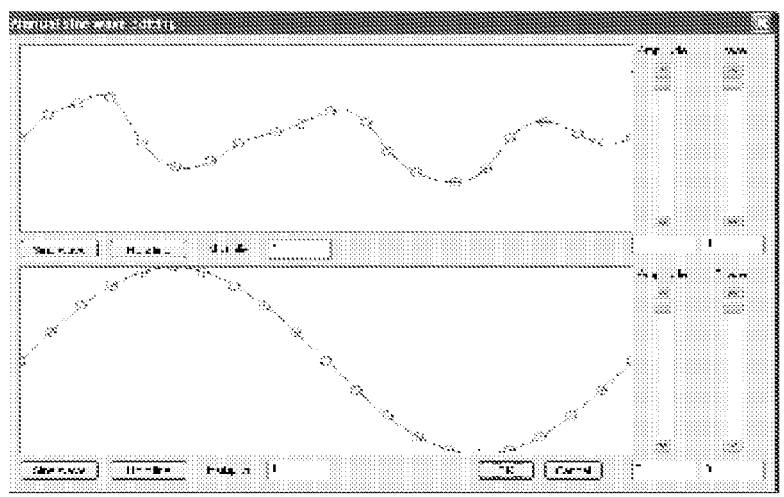
Figure 19:
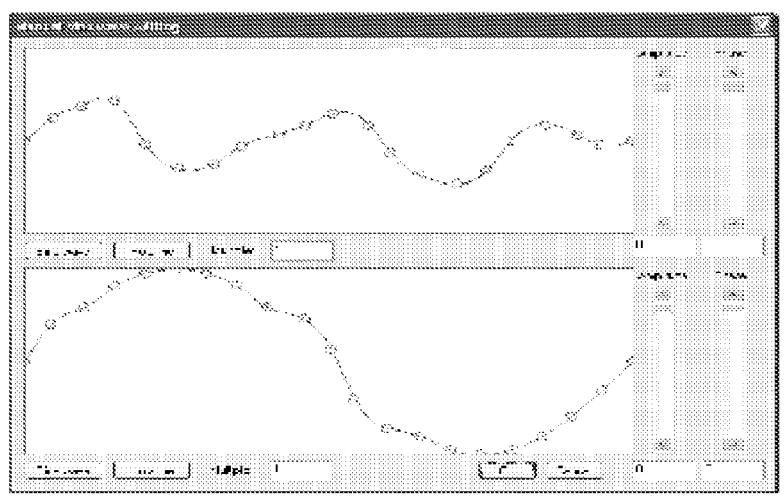

FIGS. 19A to C Show graphic user interfaces which allows the user to control manually the shape of the extra waveform to be added to the precession signal X and Y in order to correct from TEM objective lens aberration while beam is in precession mode.

DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The articles "a" and "an" are used herein to refer to one or to more than one, i.e. to at least one of the grammatical object of the article. By way of example, "a function generator" means one function generator or more than one function generator.

The recitation of numerical ranges by endpoints includes all integer numbers and, where appropriate, fractions subsumed within that range (e.g. 1 to 5 can include 1, 2, 3, 4 when referring to, for example, a number of function generator, and can also include 1.5, 2, 2.75 and 3.80, when referring to, for example, measurements). The recitation of end points also includes the end point values themselves (e.g. from 1.0 to 5.0 includes both 1.0 and 5.0)

Figure 2:
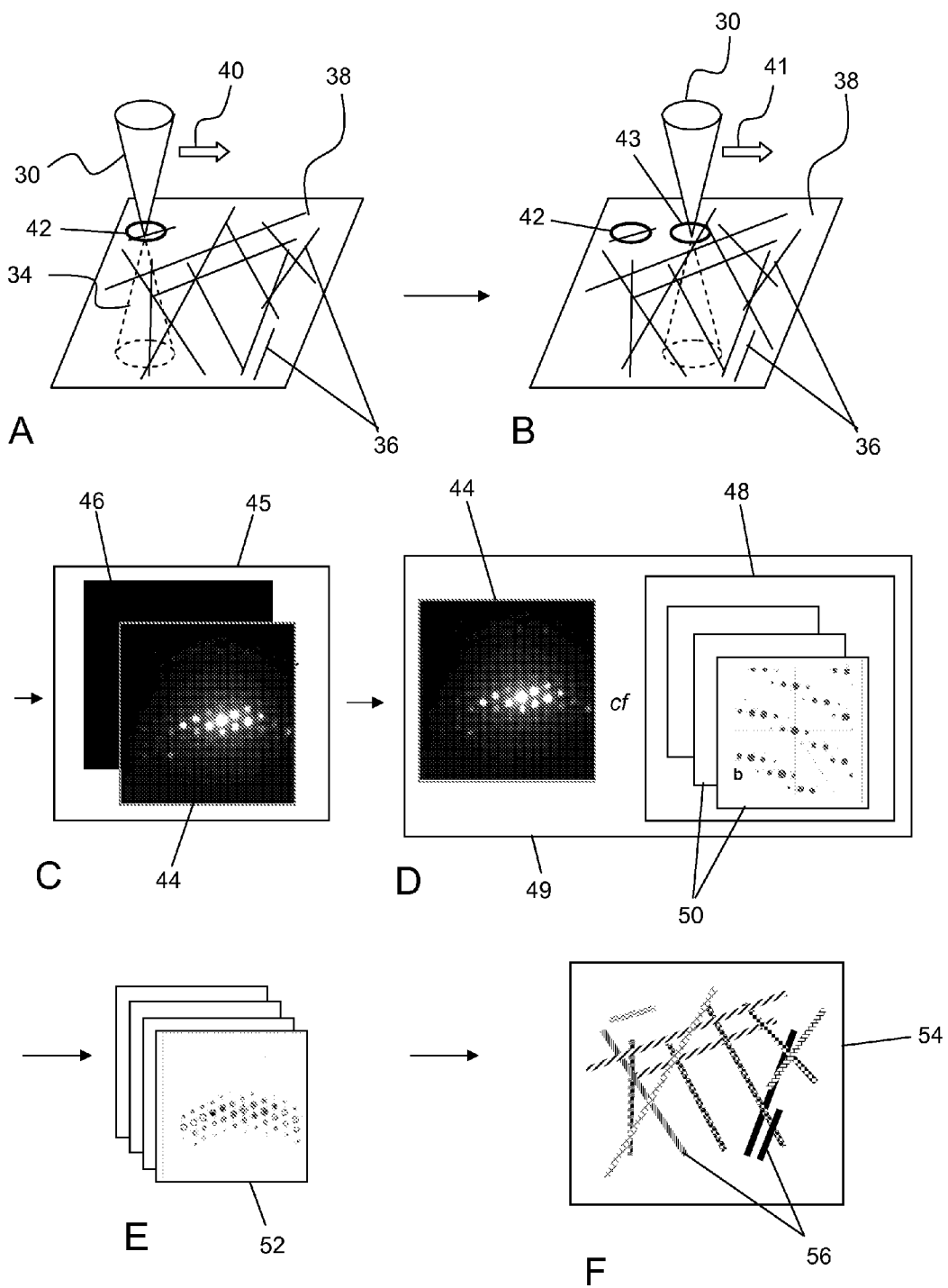

With reference to FIG. 2, one embodiment of the present invention concerns a method for calculating an orientation map of a sample of crystals using an electron diffraction device (e.g. a TEM), by providing a sample 38 comprising a plurality of said crystals 36 in different orientations, and obtaining an electron diffraction pattern 44, 46 from each of a plurality of discrete locations 42, 43 within an area of the sample 38, wherein the electron beam used to obtain the electron diffraction pattern is scanned 30 using a scanning protocol such that it converges at said location (e.g. 42 or 43) of the sample 38, in combination with a similar descanning 34 after the sample 38. In FIG. 2A, a precessed incident electron beam is directed at one location 42 while an ED pattern is acquired; subsequently, the precessed incident electron beam is advanced 40 to another location 43 (FIG. 2B) while another ED pattern is acquired. Displacement by the precessing incident electron beam 30 is continued 41 by beam scanning until the desired area of sample 38 has been acquired. The use of precession, or other scanning protocol leads to quasi-kinematical intensities, and other advantages mentioned below. A plurality 45 of ED patterns 44, 46 acquired from each location is thus obtained (FIG. 2C). Using template matching 49, each ED pattern 44 is compared against a database 48 of simulated ED patterns 50 calculated with different crystal orientations (FIG. 2D). The best simulated matches 52 allow determination of the crystal orientation for each ED pattern (FIG. 2E). Orientation information is presented as an orientation map 54, in which each different orientation 56 is plotted in a different colour, shade of grey, patterned line, or otherwise (FIG. 2F) corresponding to the location 42, 43 it was measured, thereby obtaining an orientation map 54.

Thus, one embodiment of the present invention concerns a method for calculating an orientation map of a sample 38 comprising a plurality of crystals 36 in different orientations using an electron diffraction device (e.g. a TEM), comprising the steps of:

a) providing a sample 38 comprising a plurality of said crystals 36 in different or random orientations, b) obtaining an electron diffraction, ED, pattern 44, 46 from each of a plurality of discrete locations 42, 43 within an area of the sample 38, wherein the electron beam 30 used to obtain the ED patterns is scanned over the sample 38 at every discrete location 42, 43, in combination with a beam scanning protocol as the beam converges at every discrete location 42, 43, c) determining the presence of crystals having different orientations using template matching applied the individual diffraction patterns 44, 46 obtained in b), and d) calculating an orientation map of the sample from the determination of step c).

The same technique may also be employed to obtain a phase map of the sample; the phase map may be calculated at the same time as the orientation map. Thus, another embodiment of the present invention concerns a method for calculating a phase map of a sample 38 comprising a plurality of crystals 36 in different orientations using an electron diffraction device (e.g. A TEM), comprising the steps of: a) providing a sample 38 comprising a plurality of said crystals 36 in different orientations, b) obtaining an electron diffraction, ED, pattern 44, 46 from each of a plurality of discrete locations 42, 43 within an area of the sample 38, wherein the electron beam 30 used to obtain the ED patterns is scanned over the sample 38 at every discrete location 42, 43, in combination with a beam scanning protocol as the beam converges at every discrete location 42, 43, c) determining the presence of crystals having different phases using template matching applied the individual diffraction patterns 44, 46 obtained in b), and d) calculating a phase map of the sample from the determination of step c).

Figure 3:
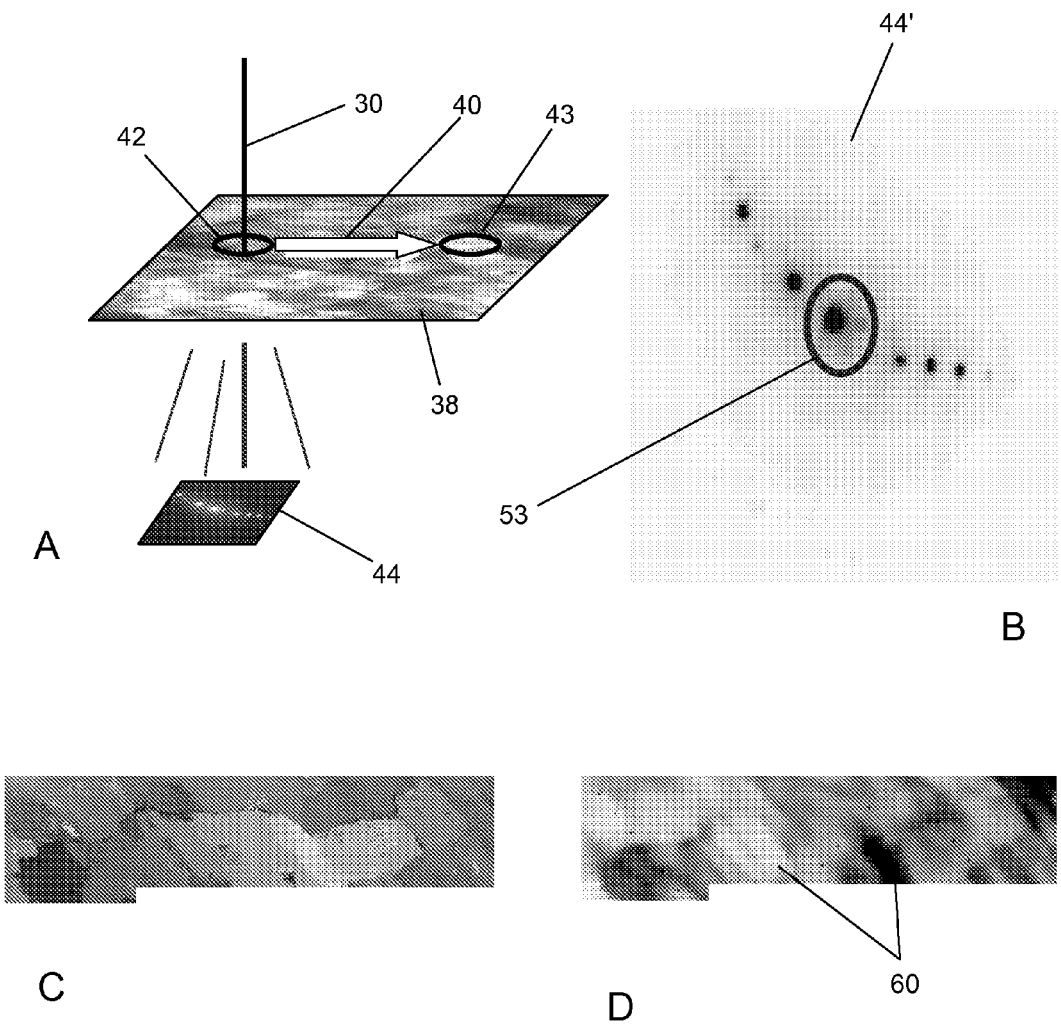

With reference to FIG. 3, another embodiment of the present invention concerns a method for calculating a relative thickness map of a sample of crystals using an electron diffraction device. During beam scanning (FIG. 3A which employs the same reference signs as FIG. 2) relative thickness maps may be created by measuring intensity of the central ED pattern by means of the CCD camera. Such experimental thickness map (equivalent to Virtual Bright Field, VBF) images will correlate with experimental orientation maps. In all those maps, digitally recorded, it will be possible in a later stage (off-line after scanning) to select ZA oriented ED precession quasi-kinematical patterns and correlate their relative intensities with common scale factor; Using the intensity of a marker which has a constant intensity regardless of the internal crystal structure—such as (but not exclusively) the central spot 53 of an ED pattern 44' shown in FIG. 3B—which intensity is proportional to the thickness of the crystal, the thickness of the crystal at the location 42, 43 may be determined. Thickness information is presented as an thickness map 58—a virtual Brightfield (VBF) map—in which each different thickness 60 is plotted in a different colour, shade of grey, patterned line, line thickness, or otherwise (FIG. 3D) corresponding to the location 42, 43 it was measured, thereby obtaining an thickness map 58 of the sample. FIG. 3D shows the corresponding orientation map. Such relative thickness maps may also created by use of other detectors including STEM imaging, HAADF imaging and zero-loss EELS imaging and can also be used in combination with beam precession and scanning as described before.

Figures 1, 4:
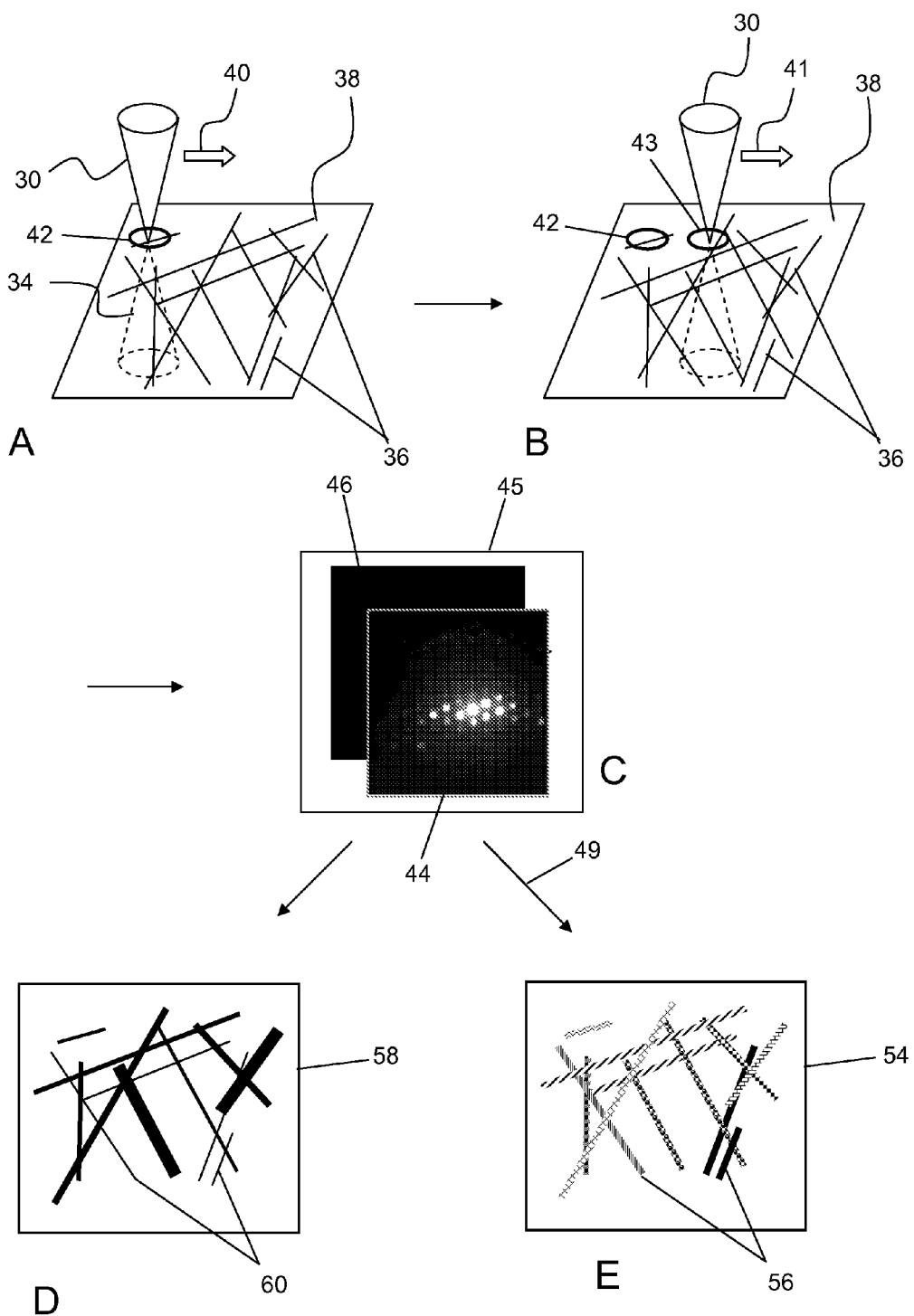
Figures 2, 4:
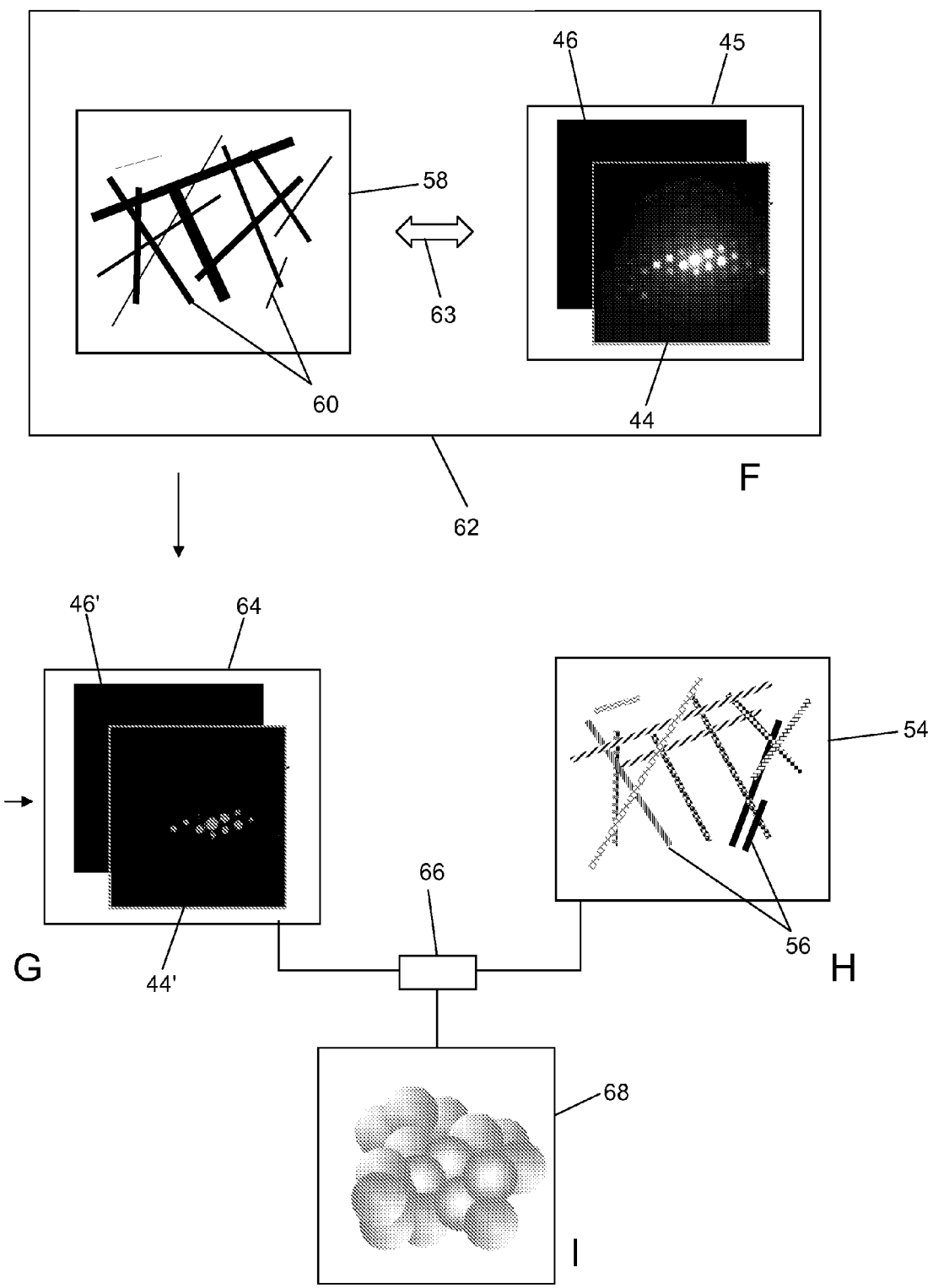

With reference to FIG. 4, another embodiment of the present invention concerns a method for random electron diffraction tomography (determining three dimensional sections of reciprocal lattice) of a crystal, by providing a sample 38 comprising a plurality of said crystals 36 in different orientations, and obtaining an electron diffraction pattern 44, 46 from each of a plurality of discrete locations 42, 43 by beam scanning within an area of the sample 38, wherein the electron beam used to obtain the electron diffraction pattern is also scanned 30 according to a scanning protocol such that it converges at said location (e.g. 42 or 43) of the sample 38, in combination with a similar descanning 34 after the sample 38. In FIG. 4-1A, the precessed incident electron beam is directed at one location 42 while an ED pattern is acquired; subsequently, the precessed incident electron beam is advanced 40 to another location 43 (FIG. 4-1B) while another ED pattern is acquired. Movement by the precessed incident electron beam 30 is continued 41 until the desired area of sample 38 has been acquired. The use of precession, or other scanning protocol leads to quasi-kinematical intensities, and other advantages mentioned elsewhere herein. A plurality 45 of ED patterns 44, 46 acquired from each location is thus obtained (FIG. 4-1C). Using template matching 49, each ED pattern 44 is compared against a database of simulated ED patterns calculated with different crystal orientations. The closest simulated matches allow determination of the crystal orientation for each ED pattern; this orientation information is used to calculate exact orientation of all randomly oriented crystals. Orientation information may optionally be presented as an orientation map 54, in which each different orientation 56 is plotted in a different colour, shade of grey, patterned line, or otherwise (FIG. 4-1E) corresponding to the location 42, 43 where it was measured, thereby obtaining an orientation map 54. From plurality 45 of ED patterns 44, 46 acquired from each location (FIG. 4-1C), the thickness of the crystal at said location is calculated; using the intensity of a marker which has a constant intensity regardless of the internal structure—such as the central TEM spot—which intensity is proportional to the thickness of the crystal, the thickness of the crystal at the location 42, 43 can be estimated. Thickness information may optionally presented as a thickness map 58—a virtual Bright field (VBF) map—in which each different thickness 60 is plotted in a different colour, shade of grey, patterned line, line thickness, or otherwise (FIG. 4-1D) corresponding to the location 42, 43 it was measured, thereby obtaining an thickness map 58 of the sample. Similar relative thickness maps may be obtained by STEM or HAADF imaging or zero loss EELS density maps corresponding to thickness variations across the sample. Such thickness information (e.g. in the form of a thickness map 58) is used to determine a common intensity scaling factor that is applied 63 to adjust (FIG. 4-2F) the intensities of the ED patterns (44, 46) in the set 45 acquired thereby factoring out the effect of crystal thickness. The set 64, of intensity-normalized ED patterns 44', 46' (FIG. 4-2G), together with the orientation information 54 (FIG. 4-2H), are used to calculate 66 the internal structure 68 of the crystal (FIG. 4-2I). It will be understood that a filtering step may be included to select those ED patterns used in the structural determination, which filtering step selects crystals of the same phase, ED patterns showing quasi-kinematical intensities, ED patterns from crystals which are either randomly perfectly oriented to various ZA, either which orientation (away from specific ZA) is accurately known It will be appreciated that parameters such as cell dimensions will have been determined beforehand. By collecting a set of 3D quasi-kinematical precession intensities from various ZA randomly oriented ED patterns (having common normalized intensities) crystal nanostructure can be solved without need for tilting individual crystals over range of angles as is required by EDPM and EDRM techniques. Same procedure applies for nanocrystals oriented to accurately known directions away from specific ZA.

Thus, another embodiment of the invention is a method for random electron diffraction tomography of a crystal sample, comprising the steps of:

a) providing a sample 38 comprising a plurality of said crystals 36 in different orientations, b) obtaining an electron diffraction, ED, pattern 44, 46 from each of a plurality of discrete locations 42, 43 within an area of the sample 38, wherein the electron beam used to obtain the ED patterns is scanned over the sample 38 every discrete location 42, 43, in combination with a beam scanning protocol as the beam converges at every discrete location 42, 43 of the sample 38, c) determining the presence of crystals having different orientations using template matching 49 applied to the individual diffraction patterns 44, 46 obtained in b), d) determining, from the individual diffraction patterns 44, 46 obtained in b), the thickness of the crystal, at the discrete location 42, 43 wherein the ED pattern was obtained, e) determining a common intensity scaling factor, from the thicknesses determined in d), and normalizing the intensities of each ED pattern, f) calculating 66 from the normalized ED patterns and orientation information, the atomic crystal structure of each separate crystal phase present in the sample.

Because the sample comprises a distribution of the crystals in different orientations, and the method obtains diffractions patterns from a plurality of locations in the sample, a distribution of diffraction patterns is obtained for a variety of crystal orientations. The random orientation of crystals in the sample, therefore, provides a range of effective tilt angles, so obviating the requirement to tilt a crystal in order to obtain the range of angles necessary for structure determination. The use of template matching provides an indication of this orientation, and also of the phase. Moreover, by scanning the electron beam (e.g. by EDPM or EDRM) before and after the sample, quasi-kinematical diffraction patterns obtained from crystals having small misorientations from the nearest zone axis appear to be perfectly oriented along those specific zone axis, The quasi-kinematical intensities of the various ED patterns from different crystals may be normalized for the different thickness, using a common scale intensity factor calculated from the intensity of the central spot from relative VBF, STEM, HAADF or zero-loss EELS relative thickness maps The method ultimately provides a complete set of 3-dimensional (3D) intensities from the total of the ZA oriented precession patterns, that permits the structure of the crystal to be solved, and establishment of a reliable 3D atomic model.

The electron diffraction device used in the present invention is any device that has the functionality of a Transmission Electron Microscope (TEM), and may be a TEM as such. FIG. 1 represents a possible arrangement of a TEM that is suitable for use in the invention. A TEM 1 comprises a gun 2, which emits electrons which pass proximal to a series of coils or lenses (5 to 16) which focus and deflect the beam. Indicated in FIG. 1 is a cross-section through the lens; since the lenses are circular coils, the view depicts two cross-sections for each coil and labeled are the right hand cross-sections for each coil. According to the example shown here, the coils are condenser stigmator coils (CSC) 5, deflection and beam tilt coils (DBTC) 6, objective stigmator and alignment coils 7, diffraction stigmator coils (DSC) 8, diffraction and intermediate alignment coils (DIAC) 9, a first condenser 10, a second condenser 11, the upper part of the objective lens 12, the lower part of the objective lens 13, the diffraction lens 14, the intermediate lens 15, the projective lens 16. The CSC 5 is situated in the second condenser coil 11. The DBTC 6 contains a rotation alignment coil, a deflection coil and a beam tilt coil; it is situated in the upper part of the objective lens 12. The DIAC 9 is the last coil used for scanning the diffraction image onto the diffractometer according to one aspect of the invention. The TEM may also comprise a 35 mm port 17 through which a diffractometer or a digital (e.g. CCD or CMOS) camera of the invention may be inserted as described above. The TEM may also comprise a window in the projection chamber 20. In FIG. 1, a digital camera of the invention 19 is positioned such that it takes a diffraction image through the window of the projection chamber 20. The TEM may also comprise a fluorescent screen 21. Another aspect of the invention is an isolated condenser diaphragm and holder 3; this special diaphragm holder with isolated condenser diaphragm is used to measure the primary beam stability of the microscope and may be inserted into the C2 beam aperture. Shown also in the figure is the sample holder 4.

The sample typically comprises a plurality of crystals in random orientations, spread over the area to be acquired. For use with a TEM, the sample is spread over a sample grid at the terminal end of the TEM sample holder. As a general guidance for a TEM, the sample will have dimensions 10×10 microns and few (e.g. 1 to 10) nm thick such that it is electron beam transparent. The size of the crystals can be any, though the invention is well suited towards crystals of nanometer range. The crystals may be of the same or different thickness, they may overlap or not overlap, and may be of the same or different phases. The crystals may be symmetric or less symmetric (e.g. monoclinic, triclinic). Samples can be of any type including large metal foils having internal structure with grain and precipitates, various inorganic crystals (oxides, ceramics, catalysts, etc) and organic crystals sensitive to the electron beam radiation.

According to the invention, an electron diffraction pattern is obtained from each of a discrete plurality of locations within an area of the sample. The sample is disposed over a grid sample area, and the incident electron beam is directed to a plurality (e.g. 10, 20, 30, 40, 50, 60, 70, 80, 90, 100, 150, 200, 1000, 10000, 20000, 50000, 100000 or more) of different locations within the sample area. The term beam scanning or scanning is used herein, which refers to displacements of the incident electron beam across the sample. The displacements are preferably by a regular distance, thereby giving rise to an array or equally spaced locations across the sample surface. The electron beam scanning preferably covers the array by taking a path that covers adjacent elements sequentially (e.g. from left to right, up and down). In other words the discrete locations form an array, in which each element is exposed by sequential displacements of the electron beam. However, a random path is also within the scope of the invention. The size of the array acquired may be, for instance, of 100×100, 200×200, 300×300, 400×400, or 500×500 discrete locations. Beam scanning (displacements) may be achieved using beam deflection coils in the electron diffraction device (e.g. TEM) situated before the sample, typically controlled by a computer through an 8 or 16 bit D/A board that allows beam displacement to be executed and monitored. More particularly, it may be achieved using a scanning signal generator described elsewhere herein. The size of the steps may be a small as 1 nm, but will typically be 2, 3, 4, 5, 6, 7, 8, 9, 10, 12, 14, 16, 18, 20, 22, 24 26, 28, 30, 40, or 50 nm, or a value in the range between any two of the aforementioned values. For an electron microscope used in imaging mode, the smallest spot size may be between 1-5 nm (FEG TEM) or 20 nm (LaB6 TEM). Beam displacement is synchronized with ED pattern capture. Beam scanning as used herein may also include similar displacements of the ED pattern after the sample, achieved using beam deflection coils in the electron diffraction device (e.g. TEM) situated after the sample. Displacements after the sample correct for displacements of the ED pattern, and align the central spot in successive ED patterns at the same location.

A scanning protocol (e.g. EDPM and EDRM) which reduces the dynamical character of ED intensities is employed in the invention to obtain each diffraction pattern. The result is ED patterns that are closer to kinematical conditions i.e. quasi-kinematical ED intensities are obtained. As mentioned elsewhere, a scanning protocol is based on scanning the incident electron beam, for instance in a conical precession or pendulum motion, or other motion which converges on the discrete location of the sample area. The beam is descanned again, using a similar motion after the sample. The scanning protocol based on precession (EDPM) is described by Vincent R., Midgley, P. Double conical beam-rocking system for measurement of integrated electron diffraction intensities. *Ultramicroscopy* 53:271-282, 1994. The scanning protocol based on a pendulum motion (EDPM) is described by Sven Hovmöller PCT/SE2007/050853 Electron rotation camera. The measurement of ED intensities in a scanning protocol mode allows all ED intensities to be recorded under reduced influence from dynamical diffraction and double scattering contributions, so permitting structure analysis of improved precision.

The scanning protocol is achieved using deflection coils in the TEM situated before the sample to scan the electron beam (e.g. in a cone or pendulum) in combination with similar descanning (e.g. in an inverted cone or pendulum) of the ED pattern by means of deflection coils situated after the sample, which coils are typically controlled by a computer through an 8 bit D/A board that allows beam displacement to be executed and monitored.

The use of more elaborate scanning protocols may lead also to quasi-kinematical ED intensities. This can be achieved using deflection coils under digital control by a device described elsewhere herein, and which permits mixing of signals.

One of the possibilities of such digital signal device is the correction of the observed beam probe size. In fact virtual probe size may increase dramatically at higher precession angles (>0.5°), this increase being dependent on the objective lens spherical aberration TEM coefficient Cs and objective lens astigmatism (especially 3-fold astigmatism). In order to correct (or decrease as much as possible such effect) and to keep the probe as small as possible at high precession angle, an extra waveform may be added to the X and Y scan signal in order to perform a dynamic compensation. Three methods to generate the waveform are within the scope of the invention, viz:

Method 1: The extra waveform can be modified manually from a straight line shape or from a sine wave generated at a specific frequency with respect to the precession frequency. Any shape of waveform can be generated. At first, it generates a straight line or sine wave which can be modified manually to compensate erratic movement of the probe while precession (FIG. 19A). With a precession motion, the user may modify the shape of the added wave to X and Y scan (FIGS. 19B and C). This allows compensating any type of aberration and/or misalignment of the TEM column.

Method 2: Automatic calculation of the corrected waveform. The added waveform is automatically calculated according to the dynamic position of the probe. This is done by acquiring one or multiple pictures in the TEM at different precession angles and precession amplitudes. Knowing the coordinates x and y of the probe versus angle on the precession circle, the shape of the waveform can be calculated. Calculation is done according to Lissajous pattern. A Lissajous pattern is a graph of one frequency plotted on the y axis combined with a second frequency plotted on the x axis. Y and X are both periodic functions of time t given by equations such as $x=\sin(w*n*t+c)$ and $y=\sin w*t$. Different patterns may be generated for different values of n(period shift) and c (phase shift). The Lissajous pattern is analyzed in order to determine n and c.

Method 3: (Automatic beam centering) Having as reference TEM screen center, dynamical probe position at different precession angles and different r, theta polar coordinates in the precession circle are calculated. An extra signal is sent to the X,Y deflection coil to shift the position of the probe dynamically to compensate (counteract) X and Y movement of the probe to bring it back to the center of the screen. Automatically, the software keeps in memory the value of the extra signal and sends it to x and y coils according to the angle in the precession circle.

In order to collect individual precession ED patterns, it is preferable that, the crystals do not overlap with each other at the location where the ED pattern is acquired. This is not always possible, especially for samples comprising nanocrystals (size <5-10 nm) agglomerates. Where overlap is unavoidable, for instance in areas of highly concentrated crystals, a polycrystalline ring ED pattern will appear. Advantageously, the scanning protocol (e.g. precession) will improve pattern circular definition, and is it possible to measure ED ring intensities to characterize local (scanned) area nanostructure. Inversely, it is within the scope of the invention to create virtual dark field maps or areas of crystal that do diffract in specific orientations, or crystals belonging to same particular phase, by selecting particular rings in collected scanned digital maps.

From the diffraction patterns obtained from the plurality of discrete locations within an area of the sample, the orientations and phases of crystals in the sample may be determined. The invention makes use of a technique of template matching to expedite the process and improve its accuracy. The technique uses an algorithm that compares the recorded ED intensity patterns with pre-calculated (simulated) templates for all possible orientations. ED patterns exhibiting the best match with the simulated template indicates the most probable orientation. At the same time, the technique identifies the phase of the crystal, thereby making possible the generation of a phase map by the same method. Referring to FIG. 2 described above, electron diffraction (ED) patterns are collected, while the sample area of interest is scanned by the electron beam. Templates are generated for all orientations over the stereographic triangle. The experimental pattern acquired with the digital camera is compared to every simulated template, and a correlation indexes map shows the best match i.e. the most probably orientation.

More specifically, for the acquired ED images, its pattern is identified by calculating the degree of matching between the templates and the collected ED data, and by selecting the one with the highest correlation index. The fundamental procedure is described by Rauch, E. F., Dupuy, L. in Rapid spot diffraction pattern identification through template matching. *Arch. Metall. Mater.* 50:87-99, 2005; and by Rauch, E. F., Veron, M. in Coupled microstructural observations and local texture measurements with an automated crystallographic orientation mapping tool attached to a TEM. *J. Mater. Sci. Eng. Tech.* 36:552-556, 2005.

The templates are generated according to the technique described in Rauch, E. F., Dupuy, L. in Rapid spot diffraction pattern identification through template matching. Arch. Metall. Mater. 50:87-99, 2005, which technique is known and understood in the art. The templates can be generated in different ways without affecting the subsequent identification routine. Complete dynamical or kinematical calculations may be considered. In the simplest approach, classical geometric construction is based on the Ewald sphere. The procedure is similar to the pattern generation used by Zaefferer (S. Zaefferer, *J. Appl. Cryst.*, 33 (2000) p. 10) to display, after indexing, the result for comparison purposes with the experimental picture. Each diffraction pattern is merely considered as the intersection of the reciprocal lattice with a sphere whose diameter is the inverse of the electron wavelength. The spot intensity depends on the distance between the diffracting beam and the transmitted beam through the atomic scattering factor, the deviation from the Bragg angle, and also on observation conditions (e.g. two or multi-beams, foil thickness). Because the latter are not exactly known, especially for severely deformed materials, a precise calculation is not possible. However, an exact value of the spot intensity is not necessary for orientation identification. An estimate is sufficient. This estimate is obtained by reducing the intensity linearly with the excitation errors i.e., the deviation from the Bragg angle). A more complex relationship (inverse, square root, exponential, ...) may be used as well, without modification of the subsequent steps of the procedure. In the database, there are no intensity images, only triplets containing the coordinates and the intensity values. The excitation error used to reproduce reasonably the patterns is usually quite high: typically between 0.05 and 0.1 Å. The database is preferably calculated off-line by dedicated software. The material characteristics (crystallographic structure, lattice parameter), the experimental conditions (accelerating voltage, size of the diffraction pattern) and some adjusted features (excitation error, angular resolution) are preferably introduced. The software calculates the templates for every orientation. Typically around 2000 simulated templates are generated for cubic materials.

The efficiency of the template matching method is due to the fact that not more than two thousand templates is sufficient for an angular resolution better than 1 deg. The main advantages of this strategy are fast processing rate, indexing time that is identical for every orientation (every scanned point of the crystal) and an identification algorithm that does not depend on the crystallographic structure; again, for low symmetry materials, the processing time is only moderately increased (e.g., by a factor of two for h.c.p. materials). The technique also enables other very important features of the material under study to be extracted such as grain size, local texture, grain boundaries and precipitates. Such crystallographic aspects can also be visualized in scanning electron microscope (SEM) microscopes by a beam scanning protocol and collecting Electron Backscatter Diffraction (EBSD—based on collected Kikuchi patterns).

Identification/fingerprinting of individual grains/crystallites can be done comparing on the basis of plots containing experimental precession quasi-kinematical intensities and crystal spacings, with several crystal data Bank data (COD, ICDD, FIZ etc. ... ).

The ED patterns may be collected using a digital camera (e.g. CCD or CMOS) directed to capture the image of the pattern visualized on a TEM fluorescent screen or attached directly to STEM screen or modified screen through a window. An on-line digital camera (12-bit or more) can be used, but a dedicated external digital camera (8 bit range, 250×250 pixels picture size) that can be mounted in front of the TEM screen is preferred (E. F. Rauch, A. Duft, P. van Houtte (Ed) ICOTOM Proceedings 14, Leuven, Belgium 2005, pp 197-202) because of its higher acquisition rate (e.g. more than 100 ED patterns $sec^{-1}$, i.e. about 10 times faster than on-line digital cameras). As mentioned elsewhere, the digital camera may be CCD or CMOS based, or other.

Figure 5:
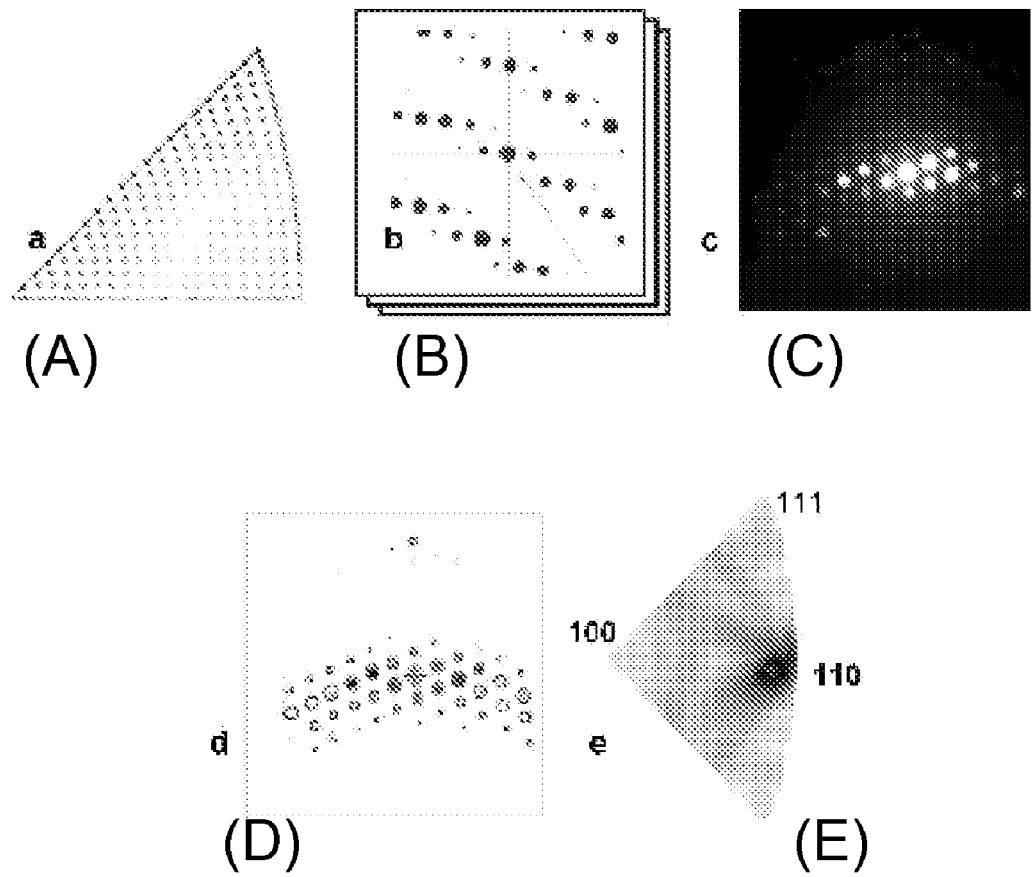

As part of the template matching procedure, a correlation index may be estimated for the individual collected ED patterns. Correlation indices for the individual ED patterns may be plotted in a projection that represents portion of the stereographic projection reduced to a double standard stereographic triangle (e.g. for cubic crystals) The resulting correlation indexes map reveals the most probable orientation for every experimental spot ED pattern. In this map the indexes are normalized by the highest value (black) (FIG. 5).

The correlation index measures a quantitative agreement between the theoretical and the experimental images, however, it may not properly weight the quality of the identification.

In a number of cases, the correlation index obtained when a well contrasted pattern is poorly recognized (e.g. second phase particle), may be the same also when the matching is correct but the background noise is important (e.g. for thick samples). Consequently, a quality index may be derived (reliability index, R), define according to Eq. 1:

$$R = 100\left(1 - \frac{Q_2}{Q_1}\right) \quad \text{(Eq. 1)}$$

where Q1 and Q2 stand for the two highest values of the correlation indexes for distinct maxima. Reliability index (R) is null if the two solutions are equivalent; by contrast R tends toward 100 when the second solution (Q2) is relatively low compared to the first one (Q1). This way, reliability maps may be created (in parallel with orientation and indexes map) where grain frontiers or crystal shapes may be clearly visualized.

Correlation indexes map are more reliable using a beam scanning protocol (e.g. precession or pendulum motion).

According to a method of the invention, the relative crystal thickness at the discrete locations where ED pattern are obtained, is determined. This is achieved by measurement of the intensity of a central spot in the ED pattern, which is proportional to the thickness of the material. The thickness information obtained can be used to create a virtual thickness map. Such experimental thickness map (a Virtual Bright Field, VBF, equivalent to a STEM-like Brightfield contrast map) may be obtained at the same time and can be correlated with orientation maps, with correlation indexes and reliability maps. Equivalent information STEM bright field or HAADF bright field or zero loss EELS maps show same qualitatively thickness sample variations with VBF maps, therefore can be used also for the same purpose. Advantageously, knowledge of the relative crystal thickness variation allows the intensities of selected ZA-oriented ED precession patterns to normalized against each other by calculating a common scale intensity factor using for example common intensity row between ED patterns. Thus, the intensities from individual precession ED patterns may be measured and compared, even though they are collected from different thickness crystals of the same crystal phase. The common scale intensity factor determined using the relative thickness map, also allows the ED intensities from experimental quasi-kinematical ZA patterns taken from various thickness crystals to be normalised, to be used for further structure determination.

The tomography (three dimensional sections of the reciprocal lattice) of the crystal is calculated using the plurality of quasi-kinematical diffraction patterns obtained for a range of crystal orientations, in which intensities have been scaled using the scaling factor determined from respective crystal thicknesses.

Cell parameters must be known beforehand, otherwise they can be estimated by simulations in comparison with experimental ED patterns. Once all experimental ED patterns (of the same phase) are indexed and their intensities collected in one set, Patterson, Fourier maps, direct methods (including maximum entropy methodology), charge flipping or any type or crystallographic algorithm may be used to find the atomic crystal model, including all atomic types and positions into the structure (including light atoms such as O).

Prior to calculation of the structure, ED patterns belonging to crystals of the same phase are selected; this may be done manually or automatically. In addition, ED patterns belonging to crystals randomly oriented to a specific ZA may also be selected. From a complete set of 3 dimensional (3D) intensities resulting from the total of the ZA oriented precession patterns, the structure may be solved, and a reliable 3D atomic model established.

The present invention offers speed advantages over methods of the art. For a typical map with an area of 300×300 pixels, it may take just a few minutes (e.g. 2 to 7 minutes) for an electron beam to scan over the sample, depending on digital camera ED capture speed. Subsequent data analysis e.g. pattern matching for orientation analysis can be performed in less 5 minutes with present desktop PC capabilities for simple cubic cells. It may take 3 to 4 times longer for tetragonal or hexagonal cells that require more templates for the same angular resolution. In view of the speed, therefore, the technique can be considered as high throughput for generation of experimental ED patterns from various nanocrystals of the same or different phases. Template matching in particular expedites the procedure to a matter of minutes compared with 8 to 10 hours using other EBSD-SEM based methods. Moreover, it has much higher angular resolution (1 deg instead of 5 deg) in comparison with other procedures (e.g. described by Dingley, D. Progressive steps in the development of electron backscatter diffraction and orientation imaging microscopy. *J. Microscopy* 21 3(3):2 14-224, 2004.) for orientation diffraction analysis where a high number of dark field patterns is collected, and then hundreds of ED patterns are reconstructed through beam rotation on the whole sample area.

For TEM studies, using spot diffraction patterns appears is an interesting alternative to Kikuchi line indexing and present computer indexing routines have been developed to extract the relevant information from them as described in Dingley, D. Progressive steps in the development of electron backscatter diffraction and orientation imaging microscopy. *J. Microscopy* 21 3(3):2 14-224, 2004, and Zaefferer, S., Schwarzer, R. A. Automated measurement of single grain orientations in the TEM. *Z. Metallkunde* 85:585-591, 1994. Such computer indexing routines concerned with spot patterns in TEM described by W. K. Pratt, *Digital Image Processing*, Wiley, New York, 1978 and A. Rosenfeld, and A. C. Kak, *Digital Picture Processing, Computer Science and Applied Mathematics*, Academic Press, NY 1976 are of general/universal application for all type of crystals even for crystals like severe deformed metals, organic and thin crystals where Kikuchi patterns are either weak or inexistent.

As a consequence of the methods of the invention, the use of beam scanning protocol (e.g. precession) in combination with acquisition from a plurality of sample locations allows a high throughput acquisition of ED patterns of beam sensitive samples, such as organic or pharmaceutically relevant crystals, even without using cryopreservation techniques.

Typically, the speed at which consecutive ED patterns can be captured, is, on the one hand, limited by the acquisition speed of the digital camera. For instance, an optical 8-bit CCD can capture in theory up to 150 ED patterns/sec, though a 12-16 bit CCD may capture only 5-10 ED patterns/sec. On the other hand, when higher speeds are reached, the fluorescent screen used in the TEM can be the limiting factor. The fluorescent screen may be susceptible to a remanence signal when consecutive patterns are rapidly projected. As a consequence, orientation or phase maps may show elongated-tail artifacts attributable to the remanence phenomenon. To solve the problem, a percentage of the intensity of the previously acquired ED pattern is subtracted from the subsequently acquired ED pattern. Thus one embodiment of the present invention is a method as described herein, further comprising the step of subtracting a percentage of the intensity of the previously acquired ED pattern from the subsequently acquired ED pattern. The percentage may be 10%, 20%, 30%, 40% or 50% or a value in the range between any two of the aforementioned values. Additionally, the obtained maps may be filtered above a threshold value. The percentage may be 10%, 20%, 30%, 40% or 50% or a value in the range between any two of the aforementioned values. Additionally, the obtained maps may be filtered above a threshold value.

In addition or alternatively, remanence due to the TEM fluorescent screen, may be reduced or eradicated by using an alternative "blue-light-fluorescent screen" which has much lower remanence properties. Alternatively, a fluorescent screen maybe avoided by incorporated the digital camera directly into the electron diffractometer (e.g. in the 35 mm port 17 of a TEM) which has its own collecting mirror screen to collect ED patterns.

According to one aspect of the invention, the electron diffraction device further comprises an energy filter configured to reduce the continuous intensity background, thereby greatly improving collected precession ED patterns. Energy filter applications in TEM are described at Werner Grogger ÆFerdinand Hofer Æ. Gerald Kothleitner ÆBernhard Schaffer 19 Jul. 2008. Experimental evidence (Example 9, FIG. 13) shows that patterns obtained with energy filtering show more, and generally more reliable reflection intensities than conventional precession patterns, improving this way matching correlation with simulated templates; this way phase identification and resulting phase/orientation maps will be much more reliable.

Another embodiment of the present is one or more devices that can be interfaced to a TEM or similar function device able to perform electron diffraction, which device adapts a TEM to measure ED patterns from a sample in accordance with the methods of the invention. The combination of the interface device of the present invention and the electron diffraction device (e.g. TEM) is known as an electron diffraction analyser herein. In one aspect of the invention, said device is capable of connecting to a TEM which is not normally equipped for measuring ED patterns according to the invention. For example, an TEM might possess a set of deflection coils located before and after the sample, but the TEM might not be equipped with a set of amplifiers to drive the coils or with a device to generate the scanning protocol (e.g. precession) or beam scanning (displacement) signals. One or more devices according to the invention provides functionality to the TEM, enabling said TEM to perform a method of the invention. In another aspect of the invention, said device is capable of connecting to a TEM which is partially equipped for measuring ED patterns. For example, a TEM might possess a set of deflection coils located before and after the sample, and with a set of amplifiers to drive the coils, but have no means to perform the scanning protocol (e.g. precession) or beam scanning (displacement) signals according to the invention. One or more devices according to the invention provides functionality to the TEM, enabling said TEM to perform a method of the invention.

In one aspect of the invention, a device(s) comprises components which enable TEM to perform one or more of the aforementioned methods separately or in combination. For example, said device(s) enables the TEM to perform the scanning protocol (e.g. precession) and/or beam scanning (ED beam displacements) and/or record an ED pattern resulting from an exposure of the sample to the beam.

The device(s) and method according to the present invention enables any TEM to be adapted to perform the methods of the invention. Examples of devices include, but are not limited to those listed below. One or more of said devices may be incorporated in a single device:

- a controller unit comprising a plurality of function generators (e.g. 4, 5, 6, 7, 8, one for each coil) each configured to output an electrical signal for activation of a deflection coil responsive to the electrical signal. The activated deflection coils directs the electron beam and ED pattern according to the desired scanning protocol (e.g. in a precession/pendulum swing motion). A controller unit is typically disposed with 8 function generators, controlled by computer processor (e.g. a PC) via different field-programmable gate arrays (FPGAs). Each generator may produce any periodic waveform of any shape. The period may be adjustable from 0 (DC) to 2000 Hertz. The phase and amplitude of each generator may be precisely adjusted to perform all necessary alignments. The function generators may also be configured to output electrical signals suitable for beam scanning i.e. displacing the incident electron beam and optionally the ED pattern by the deflection coils, however, it is also within the scope of the invention that signals controlling displacement scanning are externally provided. In such case, the controller unit may further comprise one or more mixers, operatively connected to the function generator outputs, which receive external signals (e.g. from a scanning signal generator) and mix them with the output of one or more function generators before being sent to the deflection coils. Beam scanning may be achieved by adding x and y scan signals from a scan generator to the x and y signal sent to the deflection coils. Connection between controller unit and the TEM may be achieved via copper cables, or alternatively, via optical fiber or wireless link in order to have a total galvanic isolation; this may be required in cases where it is necessary to cancel all possible interference or ground loop which can affect the beam.
- a scanning signal generator configured to generate signals for the deflection coils that displace the incident electron beam across the sample, and optionally the ED pattern after the sample, preferably in a sequential scanning motion as mentioned elsewhere herein. As mentioned elsewhere, the output from the scanning signal generator may be mixed with signals generated by the function generators,
- a relay interface which connects the output from each of the function generators to each of the deflection coils of the TEM. It allows a full disconnection of the signal to the TEM when digital device is switched off,
- a multiplexer that converts the outputs (e.g. 8 separate signals) from the function generators to a single optical signal,
- a demultiplexer to convert the single (multiplexed) optical signal into separate outputs for the TEM,
- a rack of amplifiers suitable for driving TEM coils, should suitable amplifiers be absent from the TEM. Said amplifiers may be integrated into the relay interface,
- a digital camera such as a CCD camera or CMOS camera for capture of the ED pattern,
- an analogue-to-digital means which connects to the digital camera,
- a computer having a computer readable storage means which interfaces to one or more of the above devices; the computer may be a desktop or laptop computer running Windows, UNIX, Linux which communicates with the controller unit via the FPGA. The computer may be a single computer, or two or more computers co-operatively connected. The computer may be configured for controlling the function generators, scanning signal generator, and/or recording and analysing digital camera data, and/or for generating thickness (virtual Brightfield) maps, and/or for generating orientation maps, and/ or for generating phase maps, and/or for generating correlation index maps, and/or for generating three-dimensional structures, a computer program stored on a computer readable means for controlling the function generators, scanning signal generator, and/or recording and analysing digital camera data, and/or for performing template matching and/or for generating thickness (virtual Brightfield) maps, and/or for generating orientation maps, and/or for generating phase maps, and/or for generating correlation index maps, and/or for generating three-dimensional structures.

Example of configurations of the elements that comprise a device of the invention, together with a TEM, is given in FIGS. 14 to 18. Some of the devices mentioned above are shown, however, some may be absent, depending on which devices are already present in the TEM. The associated circuitry may be absent or present as determined by the skilled person and the circuitry available. Connections between the above mentioned devices may be direct or indirect; additional components may be inserted between device as known as understood by the skilled artisan.

According to another aspect of the invention, the digital camera may be positioned in a front of a window, on the 35 mm port or any port of the TEM suitable for capturing an image of an ED pattern.

In one aspect of the invention the digital camera connects to the computer directly or via an analogue to digital converter.

According to one aspect of the invention, the computer controls the scanning protocols and/or beam scanning (ED beam displacement) and records the ED patterns from the digital camera.

All ED intensity data that are measured by the system can be automatically controlled via computer, which after performing various mathematical operations for crystal structure refinement will automatically propose to the user one (or several) crystallographic models for the studied sample.

Another aspect of the present invention is a TEM comprising one or more of the devices disclosed herein. Another aspect of the present invention is a TEM capable of performing one or more of the methods of the present invention. Another aspect of the present invention is an TEM comprising one or more of the devices disclosed herein, capable of performing one or more of the methods of the present invention.

Another embodiment of the present invention is a device suitable for interfacing with a TEM, enabling said TEM to measure ED patterns of a sample according to the methods, comprising a controller unit.

Another embodiment of the present invention is a device suitable for interfacing with a TEM, further comprising a scanning signal generator.

Another embodiment of the present invention is a device as described above further comprising a digital camera.

Another embodiment of the present invention is a device as described above further comprising a computer having a computer readable storage means as described above.

Another embodiment of the present invention is a TEM capable of performing a method as described above.

Another embodiment of the present invention is an TEM comprising a device as described above.

The present invention is a method and device that can interface to any TEM of the art or future TEM that enables said TEM to rapidly determine the structure of a crystal sample, and generate orientation, thickness, phase and correlation index maps.

Figure 14:
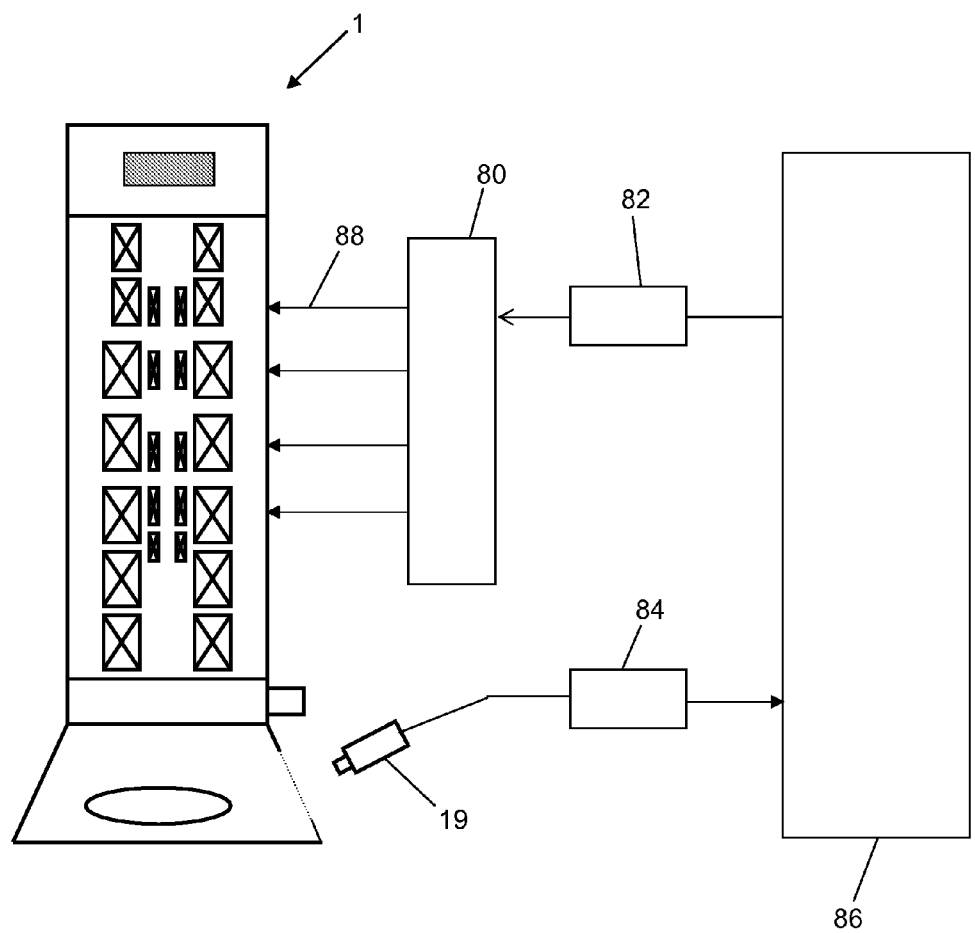

FIG. 14 shows a possible arrangement of an electron diffraction analyzer (i.e. a device of the invention linked to a TEM) that suitable for performing a method of the invention. The TEM 1 is the same as that in FIG. 1. A controller unit 80 is connected to the TEM by a plurality of electrical cables 88, and is configured to provide signals to the TEM for control of the deflection coils, for instance, the DBTC (for controlling precession) and to the DIAC (for controlling scanning and descanning of the diffraction image). The controller unit in turn is controlled by digital signals from a computer 86, which are converted from the analogue form using a D/A converter 82. The digital camera 19 is connected to a frame acquisition unit 84 which digitizes images therefrom, where they are received by the computer 86. The computer 86, by virtue of a computer program, controls the scanning protocols (e.g. precession, pendulum swing) by using deflector coil situated before the sample, and the descanning pattern by using deflection coil situated after the sample. It also controls beam scanning i.e. displacements of the incident ED beam for example, in coverage of an arrayed area of sample, and optionally complementary displacements of of the ED pattern. The computer 86 also synchronizes beam scanning with scanning protocols, and with image capture. The computer may also perform imaging processing.

Figure 15:
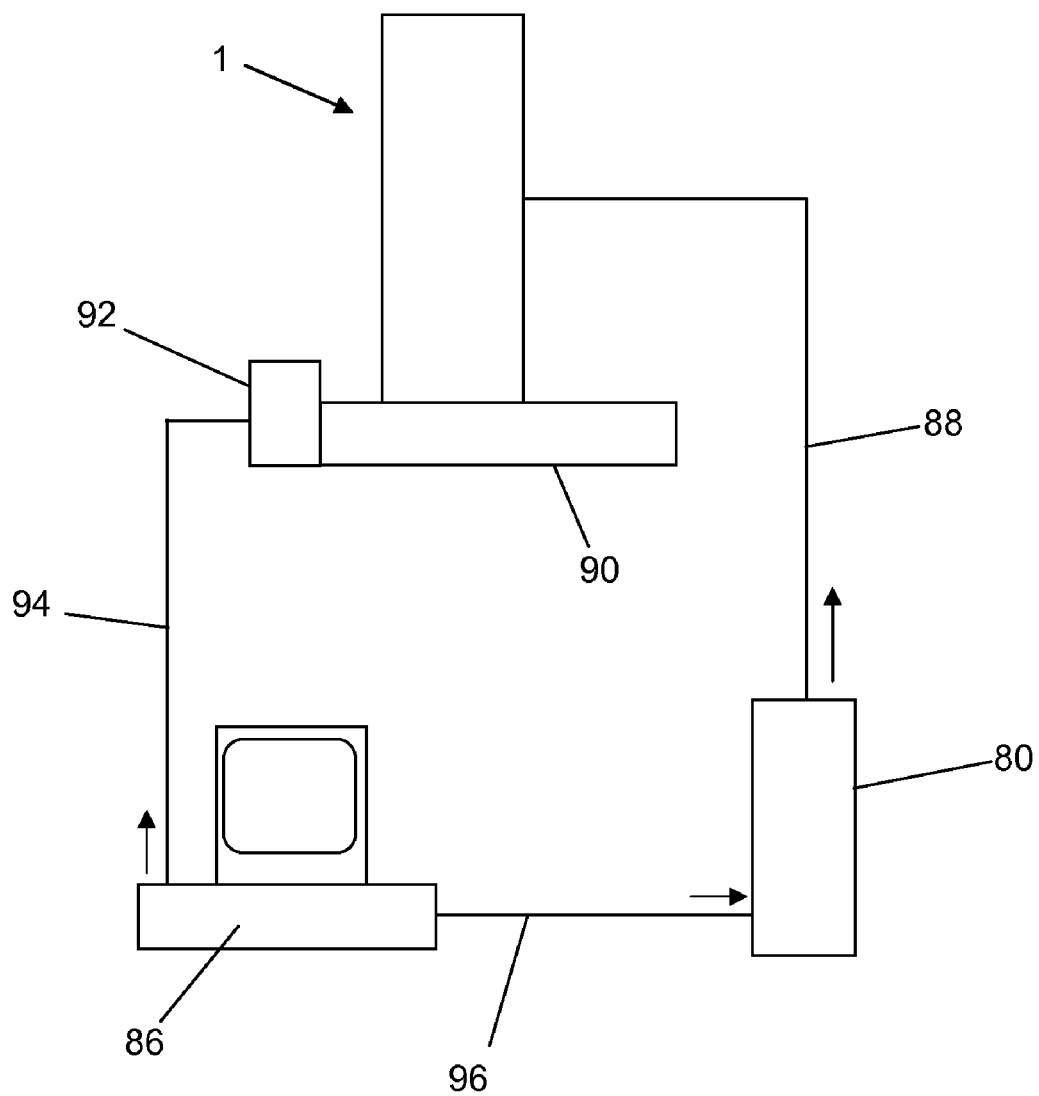

FIG. 15 shows a device-block arrangement of an electron diffraction analyzer suitable for use in a method of the invention. The TEM 1 is mounted on a TEM table 90 which incorporates a manual interface 92 e.g. a set of buttons or keyboard with which the user interacts. The deflection coils of the TEM 1 are connected, directly or via an interface, to the controller unit 80 with electrical cables 88; typically eight TEM deflection coils are controlled. The controller unit 80 is connected to a computer 86, e.g. a desktop or laptop computer running Windows, UNIX, Linux, MacOS or other operating system via a computer serial cable (e.g. Firewire cable). The manual interface 92 is connected to the computer 86 via a computer serial cable (e.g. USB cable). In this embodiment, the controller unit 80 generates the necessary signals for the scanning protocol (e.g. precessing) and beam scanning (ED beam/ED pattern displacements).

Figure 16:
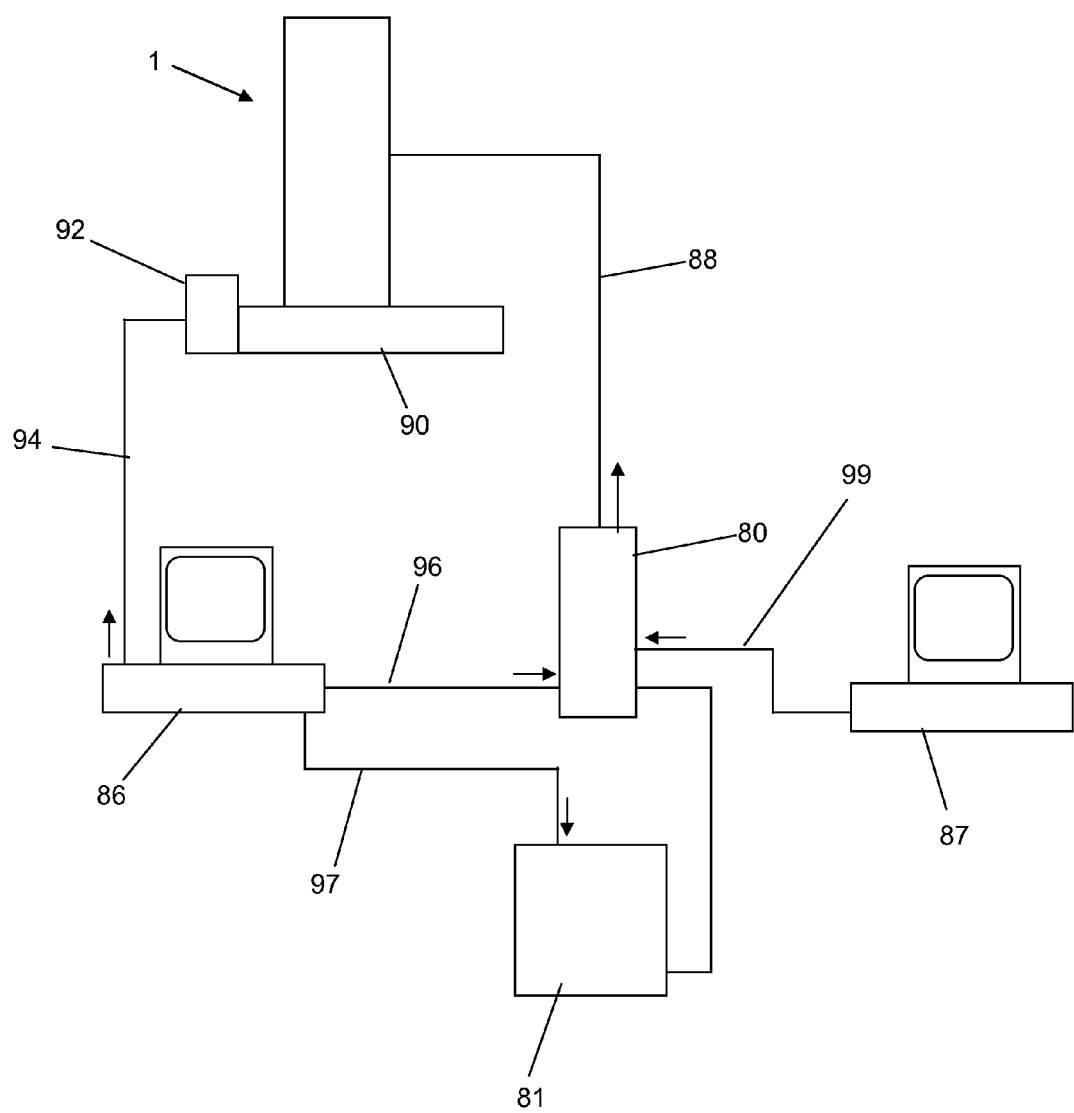

FIG. 16 shows a device-block arrangement of an electron diffraction analyzer (comprising a TEM) that permits use in a method of the invention. The device-block arrangement combines precession (scanning protocol) technique with the beam scanning technique to scan the beam across the specimen (synchronized with recording of the diffraction pattern), and the technique to descan diffraction pattern on a detector to record spot intensity precisely. The TEM 1 is mounted on a TEM table 90 which incorporates a manual interface 92 e.g. a set of buttons or keyboard with which the user interacts. The deflection coils of the TEM 1 are connected, directly or via an interface, to the controller unit 80 with electrical cables 88; typically eight TEM deflection coils are controlled. The controller unit 80 is connected to a computer 86, e.g. a desktop or laptop computer running Windows, UNIX, Linux, MacOS or other operating system via a computer serial cable (e.g. Firewire cable). The manual interface 92 is connected to the computer 86 via a computer serial cable (e.g. USB cable). In this embodiment, the controller unit 80 generates the necessary signals for the scanning protocol (e.g. precessing) patterns, while a separate computer 87 provides the necessary signals for beam scanning i.e. displacement of the incident beam across the sample area and for descanning of the displaced pattern. The scanning generator 81 is controlled by the computer 86 and its output is directed to the controller unit 80 where it is mixed with signals for scanning the diffraction pattern.

Figure 17:
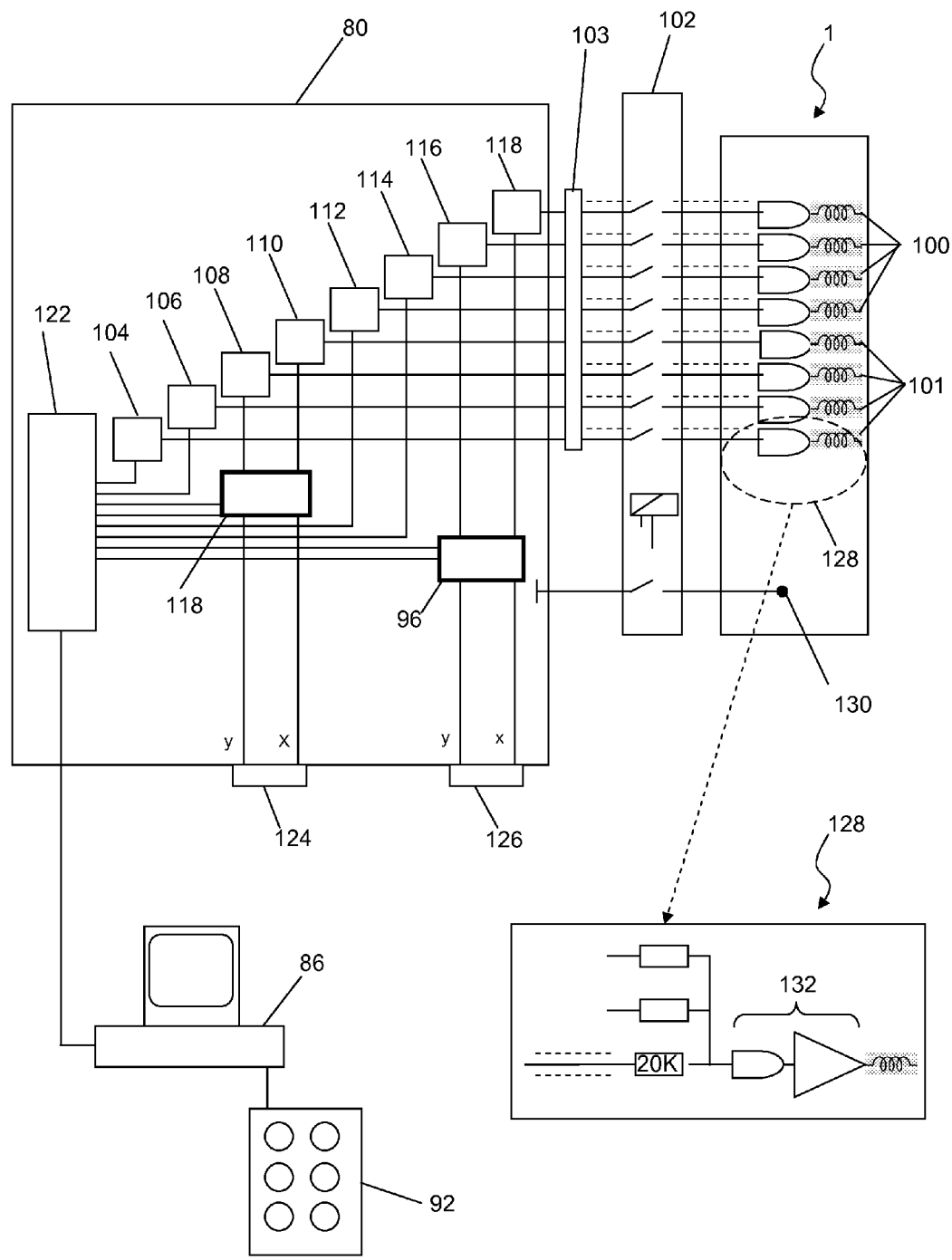

FIG. 17 shows an electron diffraction analyzer (linked to TEM) disposed with a plurality of beam tilt deflection coils 100, and beam shift deflection coils 101 each connected to a preamplifier 128, which amplifier 128 is composed of a summation preamplifier in combination with resistors as shown in the detailed view 128. Each deflection coil/amplifier set is connected to a relay disposed in a relay interface 102. The control unit 80, which connects to the relay interface 102 via an connection interface 103, comprises a plurality of function generators (104, 106, 108, 110, 112, 114, 116, 118), one for each deflection coils, each capable of generating a signal from 0 Hz (DC) to 2000 Hz. The signals, applied through deflection coils affect movement of the electron beam and pattern. The signals generated by the function generators (104, 106, 108, 110, 112, 114, 116, 118) are controlled by a field-programmable gate array (FPGA) 122, that interfaces with a computer 86, e.g. a desktop or laptop computer running Windows, UNIX, Linux, MacOS or other operating system via a computer serial cable (e.g. Firewire cable). The function generators (104, 106, 108, 110, 112, 114, 116, 118) are typically configured, under computer control, to provide the necessary scanning protocol (e.g. precession) signals; they may also provide the necessary beam and pattern scanning (displacement) signals. However, in cases where they do not provide the latter, two mixers 118, 120, are shown which receive the output signals from a scanning signal generator 126 that provides signals to displace the incidence beam, and a second scanning generator 124 that provides signals to displace the ED pattern. The mixers mix the beam and ED pattern scanning (displacement) signals and with the precession signals, which combined signals are sent to the deflection coils.

Figure 18:
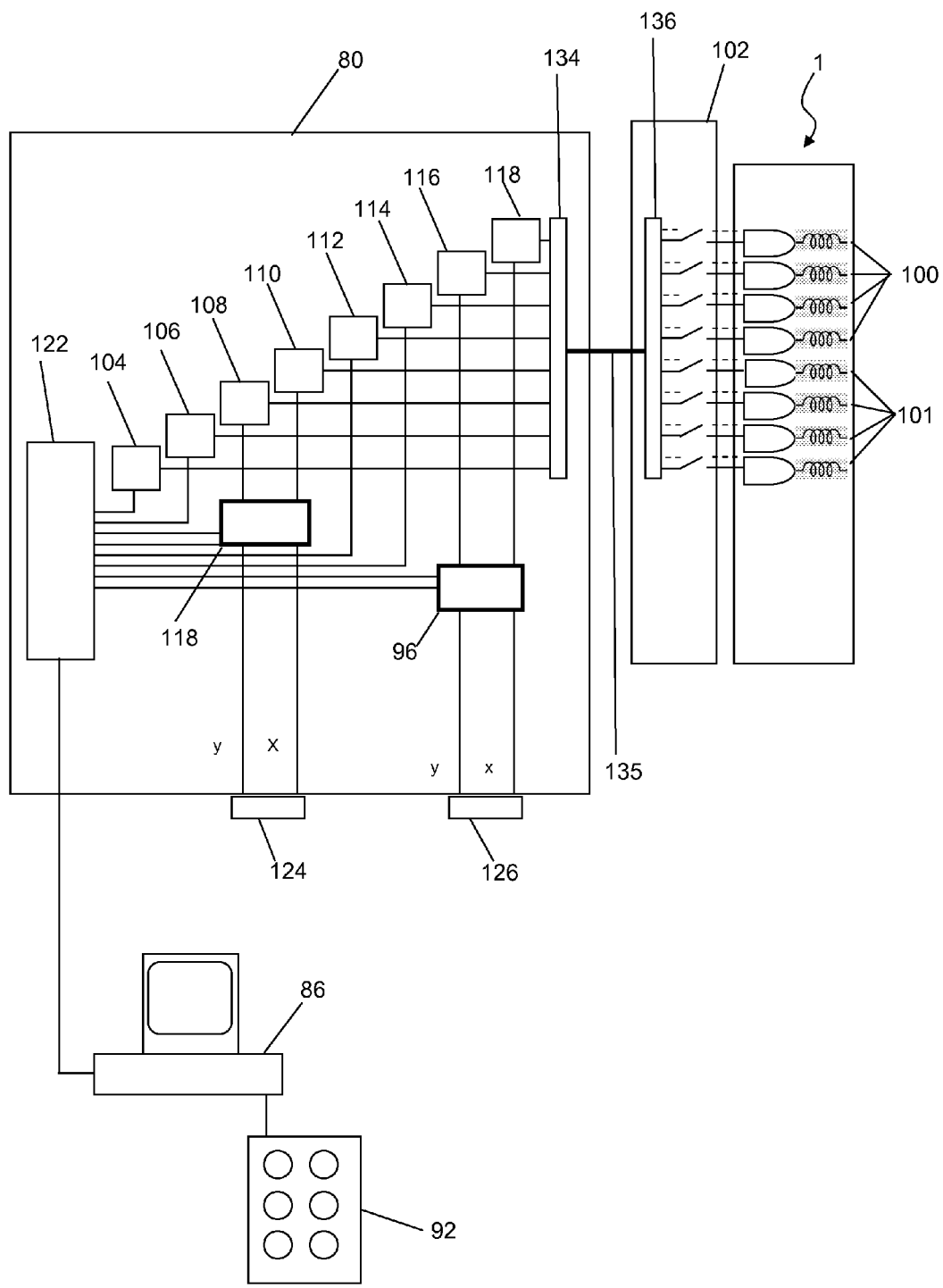

FIG. 18 is an alternative configuration of the electron diffraction analyzer of FIG. 17, whereby the TEM 1 and control unit 80 are connected by an optical fiber link 135, thereby achieving galvanic isolation between the electron microscope 1 and control unit 80. Signals from the function generators are multiplexed by a multiplexer 134, passed from the control unit 80 as an optical signal, which is demultiplexed by a demultiplexer 136 at the TEM side.

The methods and devices of the present invention provide a fast high throughput tomography by collecting several good quality quasi-kinematical ED patterns from crystals randomly oriented along ZA. The invention provides an alternative to high throughput powder X-Ray to solve crystal structures (organic/inorganic), polymorph and amorphous phase screening, without need of any specific single tilt, double tilt, cryo or any dedicated TEM holder. It can be performed with any general TEM/ED diffraction device with sample insertion facility.

EXAMPLES

Example 1

An example of template matching to determine the orientation of crystals in a sample of nanocrystalline copper is depicted in FIG. 5. FIGS. 5A and 5B show simulated templates generated for all orientations over the stereographic triangle. Shown in FIG. 5C is the experimental ED pattern acquired using a TEM equipped with a CCD camera of one location in the sample of nanocrystalline copper. The ED pattern was compared to every simulated template; shown in FIG. 5D is a matching template superimposed with circles from the experimental ED pattern. A correlation indexes map was generated as shown FIG. 5E showing the best match, i.e. the most probable crystal orientation at the point of acquisition.

Example 2

Figure 6:
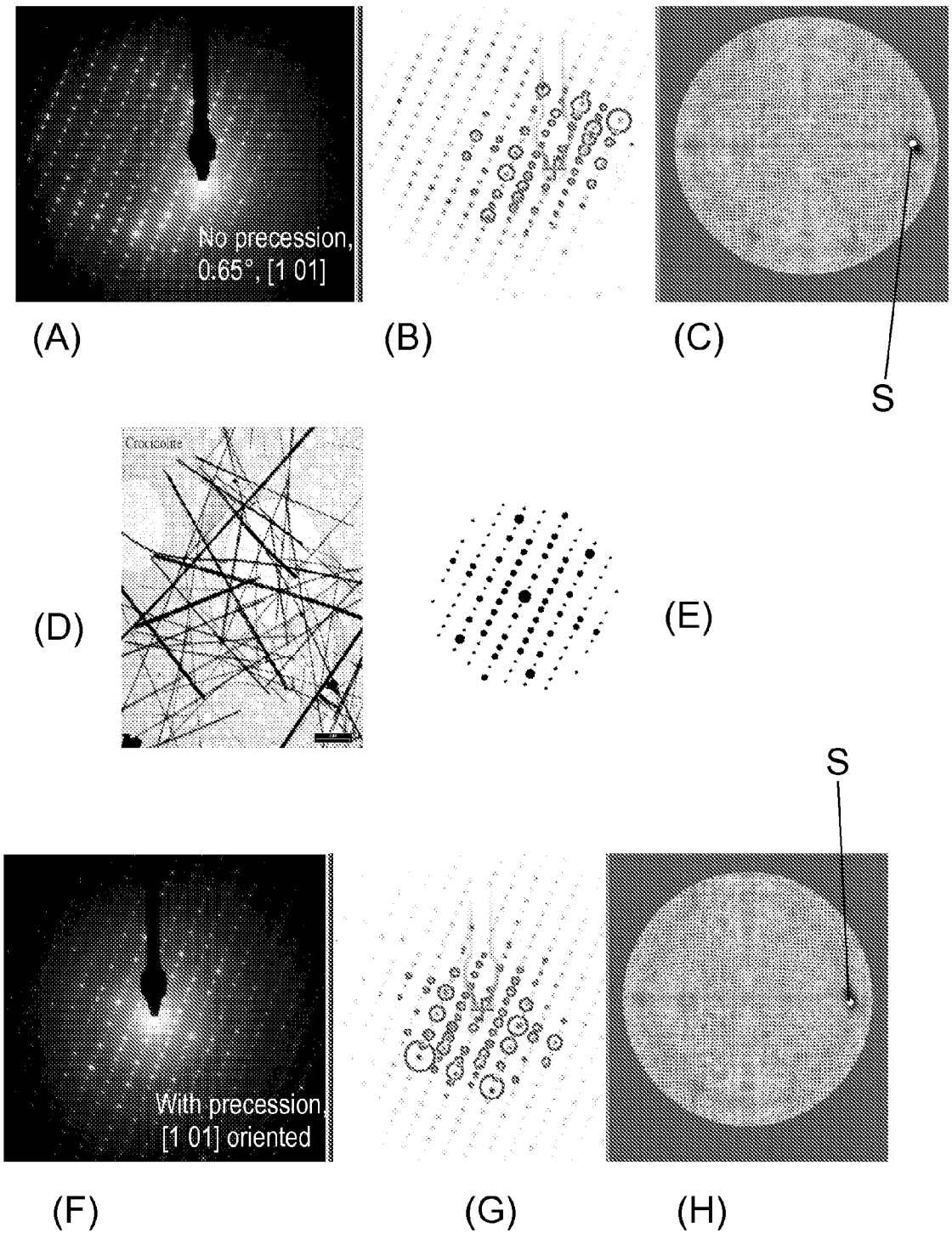

An example of template matching to determine the orientation of crystals in a sample of asbestos fiber crystals is depicted in FIG. 6 when a scanning protocol (precession) is not used compared with when it is used. Beam scanning is used in both cases. An experimental ED pattern was first acquired using a TEM at a location in the sample of asbestos fiber crystals with precession not used, resulting in an ED pattern shown in FIG. 6A captured by a CCD camera. The ED pattern was compared to every simulated template; shown in FIG. 6B is a matching template superimposed with circles from the experimental ED pattern. A corresponding correlation index map was generated, with the orientation indicated with a white spot (S), as shown in FIG. 6C. According to matching, ED pattern is 0.65° misoriented in relation to the nearest ZA [1 01]. An experiments ED pattern was then acquired at the same location in the sample of asbestos fiber crystals with precession used, resulting in an ED pattern shown in FIG. 6F captured by a CCD camera. The ED pattern was compared to every simulated template; shown in FIG. 6G is a matching template superimposed with circles from the experimental ED pattern. A corresponding correlation index map was generated, with the orientation indicated with a white spot (S), as shown in FIG. 6H. According to the matching ED pattern is now—thanks to precession—perfectly oriented along [1 01] ZA. From the entire sample, a TEM image was generated of the asbestos fiber crystal sample, as depicted in FIG. 6D. The simulation of [1 01] zone axis is shown in detail in FIG. 6E.

Example 3

Figure 7:
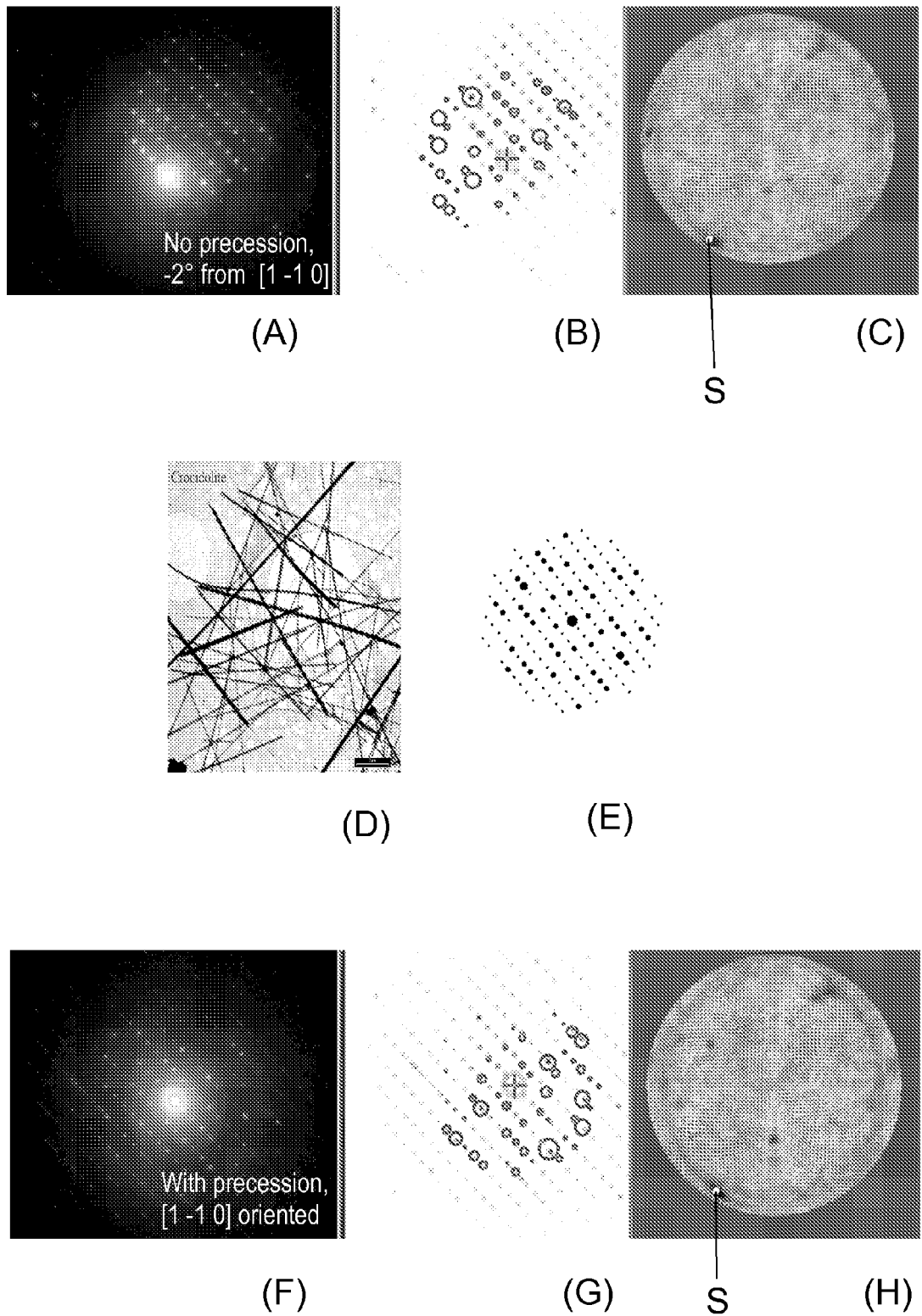

A further example of template matching to determine the orientation of crystals in a sample of asbestos fiber crystals is depicted in FIG. 7 employing beam scanning, when a scanning protocol (precession) is not used compared with when it is used. Beam scanning is used in both cases. An experimental ED pattern was first acquired using a TEM at a location in the sample of asbestos fiber crystals with precession not used, resulting in an ED pattern shown in FIG. 7A captured by a CCD camera. The ED pattern was compared to every simulated template; shown in FIG. 7B is a matching template superimposed with circles from the experimental ED pattern. A corresponding correlation index map was generated, with the orientation indicated with a white spot (S), as shown in FIG. 7C. According to matching ED pattern is −2° misoriented in relation to the nearest ZA [1-10]. An experiment ED pattern was then acquired at the same location in the sample of asbestos fiber crystals with precession used, resulting in an ED pattern shown in FIG. 7F captured by a CCD camera having perfect orientation (thanks to precession) along the zone axis [1 −1 0]. The ED pattern was compared to every simulated template; shown in FIG. 7G is a matching template superimposed with circles from the experimental ED pattern. A corresponding correlation index map was generated, with the orientation indicated with a white spot (S), as shown in FIG. 7H. From the entire sample, a TEM image was generated of the asbestos fiber crystal sample, as depicted in FIG. 7D. The simulation of zone axis [1 −1 0] is shown in detail in FIG. 7E.

Example 4

Figure 8:
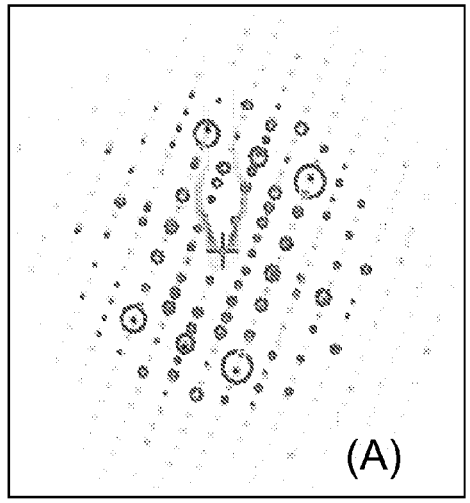
Figure 8:
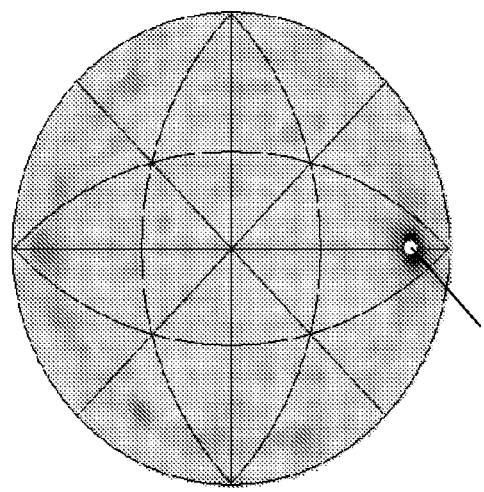
Figure 8:
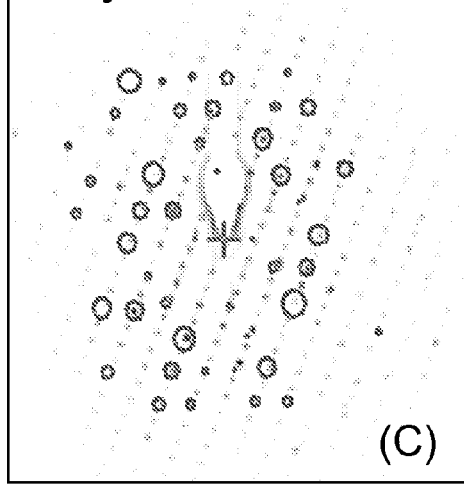
Figure 8:
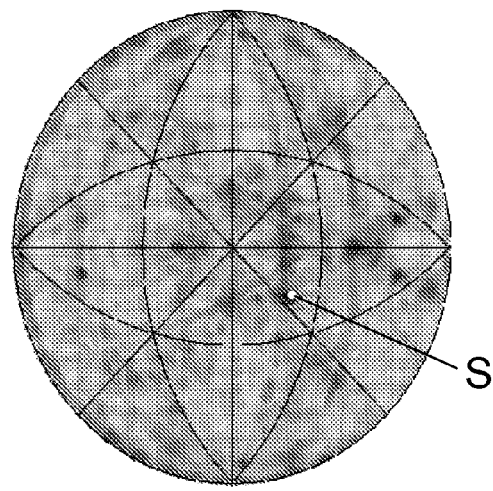
Figure 8:
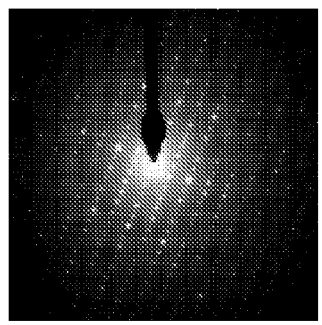

An example of template matching to determine the phase of asbestos crystal in a sample of asbestos fiber crystals is depicted in FIG. 8. Experimental ED pattern of unknown crystal asbestos phase was acquired using a TEM and precession (see ED pattern, FIG. 8E) The best pattern matching for this ED pattern (FIG. 8A) indicated a crocidolite phase. A corresponding correlation index map was generated, with the orientation indicated with a white spot (S), as shown in FIG. 8B. By contrast, the best pattern matching (FIG. 8C) for chrysotile phase shows a lower index, therefore less probability for that phase. A corresponding correlation index map was generated, with the orientation indicated with a white spot (S), as shown in FIG. 8D. lattices and cells of both monoclinic phases crocodolite and chrysotile asbestos are known from bibliography.

Example 5

A comparison of ED patterns obtained from a mayentite crystal $Ca_{12}Al_{14}O_{33}$ in arbitrary orientation when a scanning protocol (precession) of the ED beam and pattern is not used (FIG. 9A) compared with when it is used (FIG. 9B). Beam scanning is used in both cases.

Example 6

Figure 10:
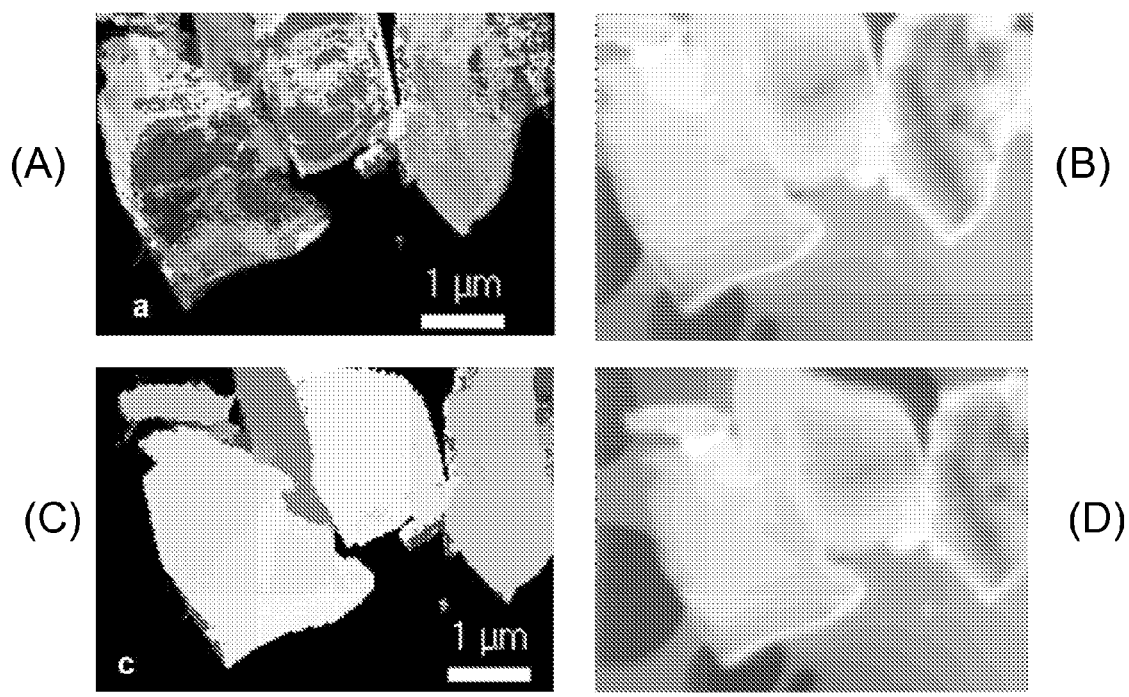

A sample of mayenite crystals was measured according to the methods of the invention in order to obtain an orientation map and thickness map (virtual Brightfield map), when a scanning protocol (with precession) is used and not used. Beam scanning is used in both cases. The total acquisition time acquisition time was 50 minutes at a rate of 10 frames per second captured by a CCD camera. The electron beam was displaced in 28 nm steps, and in a 200×150 array. FIG. 10A shows an orientation map obtained with beam scanning without precession and FIG. 10B shows a virtual bright field map also obtained at the same conditions The pattern shows many random fluctuations in greyscale intensity, indicative of frequently misindexed patterns. FIG. 10C shows an orientation map obtained with beam scanning and precession of 0.35 deg, and FIG. 10D shows a virtual bright field map also obtained at the same conditions. All other parameters (e.g. spot size, step size, camera setting, acquisition frequency, etc.) were similar. It may be noticed that orientation map quality increases dramatically with precession: true uniform orientations are depicted within each grain.

Example 7

A sample of 430 stainless steel containing precipitates of carbide $M_{23}C_6$ with an fcc structure (a=1.062 nm) and hexagonal nitride $Cr_2N$ precipitates (a=0.483 nm, c=0.451 nm), where neither the shape nor the size of precipitates help to distinguish between them. The sample was measured according to the methods of the invention in order to obtain an orientation map and phase map, where a scanning protocol (precession) was used and not used. Beam scanning is used in both cases.

The electron beam was displaced in 22 nm steps, and in a 200×300 array. FIG. 11A shows an orientation map obtained with beam scanning without precession and FIG. 11B shows a phase map also combining beam scanning without precession i.e. standard mode is utilised. The acquired phase map (FIG. 11B) without precession show ambiguous identification for two of the precipitates, each grain showing two shades of grey. FIG. 11C shows a phase map obtained by combination of beam scanning with precession of 0.3 deg, showing areas of the carbide and nitride precipitates as more continuous regions, so indicating that phase identification is reliable with precession.

Example 8

A TEM replica virtual Bright field map (FIG. 12A) was obtained showing a remanence effect at 44 frames per second owing to persistence of the image on the fluorescent screen. A similar remanence effect was seen for the corresponding correlation index map (FIG. 12B). The effect of subtracting a percentage of the previously acquired ED pattern, and generating a Bright field map therefrom is shown in (FIG. 12C); the effect of filtering the index correlation map above a threshold value is shown in (FIG. 12D).

Example 9

A mayenite crystal in an arbitrary orientation was acquired using a TEM in precession mode (1° precession angle) without (FIG. 13A) and with (FIG. 13B) an energy filter. The energy filter shows more reflection intensities than without precession.

The invention claimed is:

1. A method for electron diffraction tomography of a crystal sample, comprising:
    a) providing a sample comprising a plurality of said crystals in random orientations;
    b) obtaining an electron diffraction, ED pattern from each of a plurality of discrete locations within an area of the sample, wherein an electron beam used to obtain the ED patterns is scanned across the sample, in combination with a beam scanning protocol as the beam converges at every discrete location of the sample;
    c) determining different crystal orientations in the sample using template matching applied to the individual ED patterns obtained in b);
    d) determining, from relative thickness maps obtained as virtual bright field, STEM bright field, HAADF or zero loss EELS thickness maps, the relative crystal thicknesses at the discrete locations wherein the ED pattern were obtained;
    e) determining a common intensity scaling factor from the relative thickness determined in d), and normalizing the intensities of individual ED patterns from discrete locations; and
    f) calculating the atomic crystal structure of the randomly oriented crystals from the three dimensional set of normalized ED patterns and orientation information.

2. The method according to claim 1, wherein the scanning of the electron beam across the sample, in combination with the scanning protocol is achieved using deflection coils in the TEM situated before the sample to scan the electron beam in combination with similar descanning of the ED pattern using deflection coils situated after the sample.

3. The method according to claim 1, wherein the electron beam scanning protocol is a beam precession protocol or a beam rotation protocol, or other scanning mode protocol leading to a quasi-kinematical diffraction pattern.

4. A device for interfacing with a TEM, for adapting said TEM for performing in a method according to claim 3, configured to:
    a) obtain an electron diffraction pattern from each of a plurality of discrete locations within an area of a sample comprising a plurality of said crystals in random orientations, wherein the electron beam used to obtain the electron diffraction pattern is scanned in precession mode protocol, or other protocol, such that it converges at the discrete location of the sample, in combination with a similar descanning after the sample;
    b) determine the crystal orientations using template matching applied to the individual diffraction patterns obtained in a);
    c) determine, from relative thickness maps obtained as virtual bright field, STEM bright field, HAADF or zero loss EELS thickness maps, the relative crystal thicknesses at the discrete locations wherein the ED pattern were obtained;

d) determine a common intensity scaling factor, from the relative thickness determined in c), and normalize the intensities of individual ED patterns from discrete locations; and e) calculate the atomic crystal structure of the randomly oriented crystals from the three dimensional set of normalized ED patterns and orientation information.

5. A device according to claim 4, further configured for additional or alternative identification or fingerprinting of individual grains or crystallites using plots containing experimental precession quasi-kinematical intensities and crystal spacings, which are compared with crystal data Bank data.

6. A device according to claim 4 further configured to combine beam scanning with ED energy filtering to enhance identification or fingerprinting of individual grains or crystallites and to obtain better quality orientation phase maps.

7. A device according to claim 4 further configured for high throughput rates.

8. The method according to claim 1, wherein the discrete locations form an array, and each array element is exposed by sequential displacements of the electron beam.

9. The method according to claim 1, wherein ED patterns that do not belong to crystals of the same phase are not used in f).

10. The method according to claim 1, wherein:
the beam scanning is controlled by x and y scan signals generated by a scan generator which control x and y deflection coils in the TEM; and
a waveform is added to the x and y scan signal to perform dynamic compensation of observed beam probe size.

11. The method according to claim 1 further comprising additional or alternative identification or fingerprinting of individual grains or crystallites using plots containing experimental precession quasi-kinematical intensities and crystal spacings, which are compared with crystal data Bank data.

12. The method according to claim 1 wherein beam scanning and ED energy filtering are combined to enhance identification or fingerprinting of individual grains or crystallites and to obtain better quality orientation phase maps.

13. The method according to claim 1 wherein said method is performed at a high throughput.

* * * * *